(12) United States Patent
Haldar et al.

(10) Patent No.: US 12,329,760 B2
(45) Date of Patent: Jun. 17, 2025

(54) METHODS AND COMPOSITIONS FOR TARGETING RETINOIC ACID FOR SOLID TUMOR IMMUNOTHERAPY

(71) Applicant: THE TRUSTEES OF THE UNIVERSITY OF PENNSYLVANIA, Philadelphia, PA (US)

(72) Inventors: Malay Haldar, Wynnewood, PA (US); Samirkumar Devalaraja, Acton, MA (US)

(73) Assignee: The Trustees of the University of Pennsylvania, Philadelphia, PA (US)

( * ) Notice: Subject to any disclaimer, the term of this patent is extended or adjusted under 35 U.S.C. 154(b) by 609 days.

(21) Appl. No.: 16/869,356

(22) Filed: May 7, 2020

(65) Prior Publication Data
US 2020/0352958 A1 Nov. 12, 2020

Related U.S. Application Data

(60) Provisional application No. 62/846,160, filed on May 10, 2019.

(51) Int. Cl.
A61K 31/5513 (2006.01)
A61K 31/505 (2006.01)
A61P 35/00 (2006.01)
C07K 16/24 (2006.01)
C07K 16/28 (2006.01)
G01N 33/574 (2006.01)

(52) U.S. Cl.
CPC ........ *A61K 31/5513* (2013.01); *A61K 31/505* (2013.01); *A61P 35/00* (2018.01); *C07K 16/244* (2013.01); *C07K 16/2818* (2013.01); *C07K 16/2827* (2013.01); *G01N 33/574* (2013.01); *G01N 2333/70567* (2013.01)

(58) Field of Classification Search
CPC .............. A61K 31/505; A61K 31/5513; A61K 39/3955; A61K 2039/505; A61P 35/00; C07K 16/24; C07K 16/2818; C07K 16/2827; C07K 16/244
See application file for complete search history.

(56) References Cited

U.S. PATENT DOCUMENTS

2001/0003780 A1* 6/2001 Tramposch ............ A61K 31/38
562/490
2016/0324874 A1 11/2016 Leung
2017/0354623 A1* 12/2017 Chandraratna ........ A61K 45/06
2017/0369841 A1 12/2017 Sugiyama

FOREIGN PATENT DOCUMENTS

WO WO-2005062972 A2 * 7/2005 ........... C07K 16/244
WO WO-2017049110 A1 * 3/2017 ........... C07C 403/16

OTHER PUBLICATIONS

Cunningham, T. J. et al., "Mechanisms of retinoic acid signalling and its roles in organ and limb development", Nat. Rev. Mol. Cell Biol. 16, 110-123 (2015).
Devalaraja et al., "Abstract B26: Sarcoma microenvironment blocks DC but promotes macrophage differentiation from tumor infiltrating monocytes", DOI: 10.1158/1557-3265.SARCOMAS17-B26, published Jan. 2018, 4 pages.
Haldar, "Abstract: NIH RePORT. Regulation of Antigen Presenting Cells in the Tumor Microenvironment by Retinoic Acid", printed May 10, 2019, 2 pages.
Haldar, M. et al., "Heme-mediated SPI-C induction promotes monocyte differentiation into iron-recycling macrophages", Cell 156, 1223-1234 (2014).
Keedwell et al., "An antagonist of retinoic acid receptors more effectively inhibits growth of human prostate cancer cells than normal prostate epithelium", British Journal of Cancer (2004) 91, 580-588.
Marcato, P. et al., "Aldehyde dehydrogenase: its role as a cancer stem cell marker comes down to the specific soform", Cell Cycle Georget. Tex 10, 1378-1384 (2011).
Tang, X.-H. et al., "Retinoids, retinoic acid receptors, and cancer", Annu. Rev. Pathol. 6, 345-364 (2011).
Yang et al., "Retinoic acid receptor antagonist BMS453 inhibits the growth of normal and malignant breast cells without activating RAR-dependent gene expression", Breast Cancer Res Treat. Aug. 1999;56(3):277-91.

* cited by examiner

Primary Examiner — Sarah Pihonak
(74) Attorney, Agent, or Firm — Saul Ewing LLP; Kathryn Doyle; Justin W. Crotty

(57) ABSTRACT

The present invention relates to compositions and methods comprising a retinoic acid receptor inhibitor, a retinoic X receptor inhibitor or an inhibitor of an enzyme in the retinoic acid biosynthesis pathway for treatment of a patient having a solid tumor. In some embodiments, the solid tumor is a sarcoma.

17 Claims, 39 Drawing Sheets

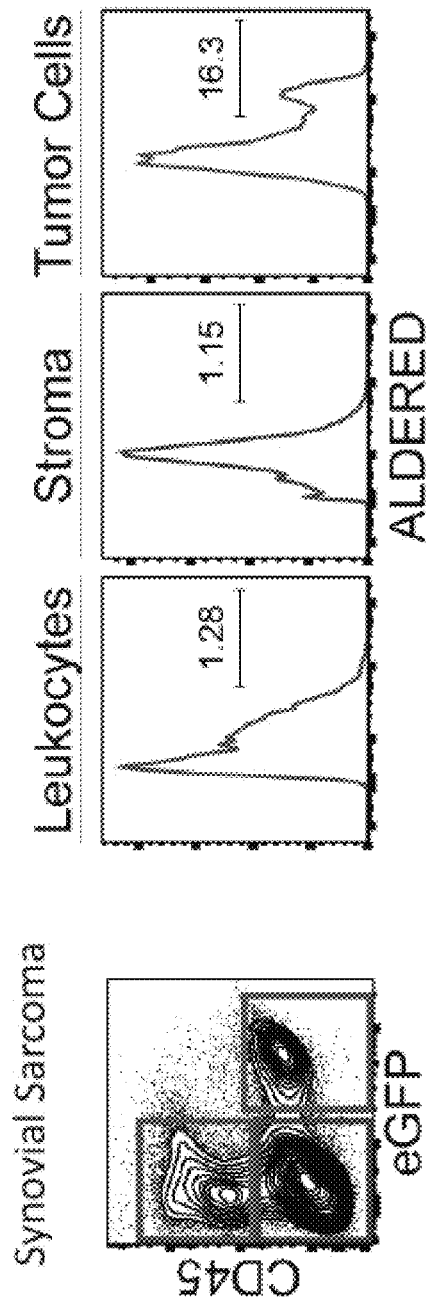
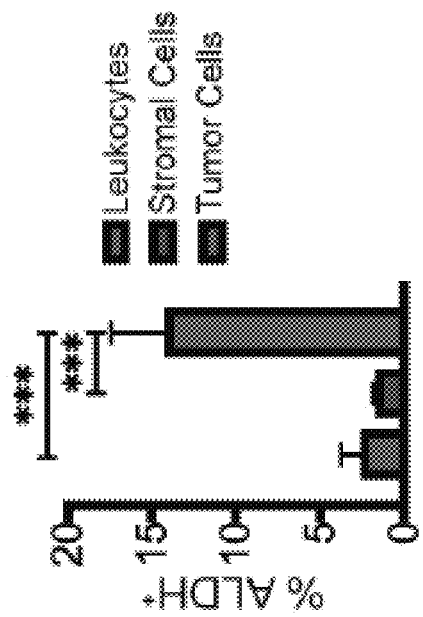
FIG. 24A
FIG. 24B

METHODS AND COMPOSITIONS FOR TARGETING RETINOIC ACID FOR SOLID TUMOR IMMUNOTHERAPY

CROSS-REFERENCE TO RELATED APPLICATION

The present application is entitled to priority under 35 U.S.C. § 119(e) to U.S. Provisional Patent Application No. 62/846,160, filed May 10, 2019, which is hereby incorporated by reference in its entirety herein.

STATEMENT REGARDING FEDERALLY SPONSORED RESEARCH OR DEVELOPMENT

This invention was made with government support under Grant No. 575883 awarded by the National Cancer Institute (NCI). The government has certain rights in the invention.

BACKGROUND OF THE INVENTION

Sarcomas are a rare but diverse group of mesenchymal malignancies. There are over 70 different molecular subtypes of sarcomas. The five year survival rate is less than 15%. Treatment is limited to surgery and radiation. Immunotherapies such as immune checkpoint blockers are ineffective in the majority of patients.

There remains a need for methods and compositions for immunotherapy to treat solid tumors such as sarcomas.

SUMMARY OF THE INVENTION

As described herein, the present invention relates to compositions and methods comprising a retinoic acid receptor inhibitor, a retinoic X receptor inhibitor, or an inhibitor of an enzyme in the retinoic acid biosynthesis pathway for treatment of a patient having a solid tumor.

In one aspect, the invention provides a method for treating a patient having a solid tumor. The method comprises administering to the patient an effective amount of a retinoic acid receptor inhibitor, a retinoic X receptor inhibitor, or any combination thereof.

In certain embodiments, the retinoic acid receptor inhibitor is selected from the group consisting of AGN 193109, BMS 195614, BMS 493, CD 2665, ER 50891, LE 135, LY 2955303, MM 11253, any salt or solvate thereof, and any combinations thereof.

In certain embodiments, the retinoic X receptor inhibitor is selected from the group consisting of HX 531, PA 452, and UVI 3003, any salt or solvate thereof, and any combinations thereof.

In certain embodiments, the method further comprises administering to the patient an immune checkpoint inhibitor. In certain embodiments, the immune checkpoint inhibitor is selected from the group consisting of an anti-PD1 antibody, an anti-PD-L1 antibody, an anti-CTLA4 antibody, any fragment thereof, and any combinations thereof.

In certain embodiments, the method further comprises administering to the patient an anti-IL13 antibody or fragment thereof.

In certain embodiments, the retinoic acid receptor inhibitor, the retinoic X receptor inhibitor, the immune checkpoint inhibitor, the anti-IL13 antibody or any combinations thereof are administered to the patient simultaneously or sequentially.

In certain embodiments, the retinoic acid receptor inhibitor, the retinoic X receptor inhibitor, the immune checkpoint inhibitor, the anti-IL13 antibody or any combinations thereof further comprise a pharmaceutically acceptable carrier or adjuvant.

In certain embodiments, the solid tumor is a sarcoma.

In another aspect, the invention provides a composition comprising a retinoic acid receptor inhibitor, a retinoic X receptor inhibitor or any combination thereof, and an immune checkpoint inhibitor.

In certain embodiments, the composition further comprises an anti-IL13 antibody.

In certain embodiments, the immune checkpoint inhibitor is selected from the group consisting of an anti-PD1 antibody, an anti-PD-L1 antibody, an anti-CTLA4 antibody, any fragment thereof, and any combinations thereof.

In another aspect, the invention provides a method for treating a patient having a solid tumor. The method comprises administering to the patient an effective amount of an inhibitor of an enzyme in the retinoic acid biosynthesis pathway.

In certain embodiments, the enzyme in the retinoic acid biosynthesis pathway is selected from the group consisting of RALDH1, RALDH2 and RALDH3.

In certain embodiments, the method further comprises administering to the patient an immune checkpoint inhibitor. In certain embodiments, the immune checkpoint inhibitor is selected from the group consisting of an anti-PD1 antibody, an anti-PD-L1 antibody, an anti-CTLA4 antibody, any fragment thereof, and any combinations thereof.

In certain embodiments, the method further comprises administering to the patient an anti-IL13 antibody or fragment thereof.

In certain embodiments, the inhibitor of an enzyme in the retinoic acid biosynthesis pathway, the immune checkpoint inhibitor, the anti-IL13 antibody or any combinations thereof are administered to the patient simultaneously or sequentially.

In certain embodiments, the inhibitor of an enzyme in the retinoic acid biosynthesis pathway, the immune checkpoint inhibitor, the anti-IL13 antibody or any combinations thereof further comprise a pharmaceutically acceptable carrier or adjuvant.

In certain embodiments, the solid tumor is a sarcoma.

In another aspect, the invention provides a composition comprising an inhibitor of an enzyme in the retinoic acid biosynthesis pathway and an immune checkpoint inhibitor.

In certain embodiments, the composition further comprises an anti-IL13 antibody.

In certain embodiments, the immune checkpoint inhibitor is selected from the group consisting of an anti-PD1 antibody, an anti-PD-L1 antibody, an anti-CTLA4 antibody, any fragment thereof, and any combinations thereof.

In another aspect, the invention provides a method of selecting a patient having a solid tumor for treatment with a retinoic acid receptor inhibitor, a retinoic X receptor inhibitor or an inhibitor of an enzyme in the retinoic acid biosynthesis pathway. The method comprises obtaining a tumor sample from a patient, detecting the expression level of a retinoic acid regulated gene in the tumor sample, and selecting the patient for treatment with a retinoic acid receptor inhibitor, a retinoic X receptor inhibitor or an inhibitor of an enzyme in the retinoic acid biosynthesis pathway if the expression level of the retinoic acid regulated gene is above that of a control.

BRIEF DESCRIPTION OF THE DRAWINGS

The following detailed description of preferred embodiments of the invention will be better understood when read in conjunction with the appended drawings. For the purpose of illustrating the invention, there are shown in the drawings embodiments which are presently preferred. It should be understood, however, that the invention is not limited to the precise arrangements and instrumentalities of the embodiments shown in the drawings.

FIG. 6C shows a series of histograms. Fibrosarcomas were generated by transplanting MCAS in a Zbtb46$^{GFP}$ mouse. The Zbtb46-GFP mouse expresses the GFP reporter molecule in dendritic cells. Histograms depict expression of Zbtb46-GFP within the indicated population (gating scheme shown in FIG. 6A and FIG. 6B). FIG. 6D shows cells corresponding to FIG. 6C (arrows).

FIG. 7A: fibrosarcomas generated in Lysm$^{Cre/+}$:Rosa$^{tdt/+}$:Zbtb46$^{gfp/+}$ mice by transplanting MCAS cells were analyzed by FCM. Headers denote gating for population shown below. Data is representative of >5 experiments. FIG. 7B: Monocytes were purified from bone marrow of Lysm$^{Cre/+}$:Rosa$^{tdt/+}$:Zbtb46$^{gfp/+}$ mice using the miltenyi monocyte isolation kit and injected directly into fibrosarcomas generated by transplanting MCAS cells into wild type B6 mice. Transplanted monocytes (tdt+) were analyzed after 6 days. Data is representative of 3 experiments.

FIGS. 8A-8B: Gene expression profile Microarray, Affymetrix Gene 1.0ST) of F4/80+CD11C-macrophages from UPS (UPS Mac) compared to various tissue resident macrophages (obtained from immgen.org). Shown are the expression of two cellular retinoic acid binding proteins CRABP1 (FIG. 8A) and CRABP2 (FIG. 8B). Y-axis: Expression levels, linear scale, mean value of 2 independent samples. PEC: Peritoneal cavity macrophage; RPM: Red pulp macrophage; BMM: Bone marrow macrophage; Alv Mac: Alveolar macrophage. FIG. 8C: Gene expression profile (Microarray, Affymetrix mouse gene 2.0) of murine SS tumors compared to surrounding muscle. Y-axis: expression levels, linear scale, mean value of 2 independent samples. Aldh1a2: Aldehyde dehydrogenase 1A2; TAM: Tumor associated F4/80+CD11Cmacrophage; DC: Dendritic cells. FIG. 8D: Liquid chromatography/mass-spectrometry based measurement of RA in murine sarcomas and surrounding muscle. Y-axis: nanograms of RA detected per milligram of tissue tested. Acitretin was used as internal standard for LC/MS. $P<0.05$ for RA levels in Tumors vs. Skeletal muscle.

FIG. 14A: Doxycycline-induced expression of RALDH3-targeting shRNA in MCASshRNA (RALDH3)-RFP tumors leads to reduced number of RFP+ (RALDH3 deficient) tumor cells in immunocompetent (C57BL/6J) but not immunodeficient (NU/J) mice. FIG. 14B: Reduced RA (via induction of RALDH3-targeting shRNA) leads to increased T cells (25% vs. 7%) in immunocompetent mice. (FIG. 14A, FIG. 14B) Mice received doxycycline (or no treatment in control group) beginning the day of tumor transplant and tumors analyzed after 13 days. Data is representative of >3 experiments with 3 or more mice per group per experiment. FIG. 14C: CRISPR/Cas9-based deletion of RALDH3 gene leads to tumor rejection in immunocompetent but not immunodeficient NU/J mice. Two distinct exons (2 and 7) were targeted to establish two distinct RALDH3 knockout cell lines. Data shown is cumulative (percentage mice harboring tumors) from >3 experiments that include 50 mice (25 cas9 only, 20 Cas9+sgRNA-exon 7, and cas9+sgRNA-exon 3) immunocompetent C57BL/6J mice and 10 (5 cas9 only and 5 cas9+sgRNA-exon 7) NU/J immunodeficient mice.

FIG. 15A: MCAS tumors were labelled for RA production using the aldefluor assay. FIG. 15B: Aldefluor positive and negative cells from tumors were purified by FACS and the expression (relative to 18S) of RALDH3 quantified by RT-QPCR. Also shown is the expression of RALDH3 in vitro in MCAS cells. Data is representative of 3 independent experiments.

FIG. 16A: MCAS cells were treated in vitro with indicated agents and RALDH3 expression (relative to 18S) measured by RT-QPCR. P<0.05 between no Tx and IL4 or IL13. N=3, repeated >5 times. FIG. 16B: IL13 and IL13Rα1 staining in murine UPS. FIG. 16C: Single cell suspension from MCAS tumors were fractionated into CD45+(Leukocytes) and CD45-fraction using miltenyi magnetic columns. RT-QPCR based measurement (relative to 18S) of IL13 and IL13Rα1 transcripts were performed on fractionated cells. P<0.01 for IL13. N=3, experiment repeated twice.

FIG. 20A: MCAS cells were treated with indicated compounds and RALDH3 expression (relative to 18S) measured by RT-QPCR. P<0.01 for DMSO vs. IL13. P<0.05 for IL13 vs. IL13+BMS493. FIG. 20B: Schematic of RALDH3 regulation by RA.

FIGS. 24A-24B illustrate that the majority of RA is produced by tumor cells. ALDERED assay (EMD Millipore, SCR150) was performed on mouse synovial sarcoma (SS). Representative contour plot of eGFP+tumors cells, CD45+ leukocytes and stromal cells (Left, FIG. 24A). Representative histograms of ALDERED fluorescence in the aforementioned populations (right). FIG. 24B shows frequency of ALDH+cells within indicated parent populations (n=6 tumors).

FIGS. 25A and 25B show the frequency of ALDH+cells within indicated parent populations (n=4 UPS and n=10 FS)]. FIG. 25C shows the histogram from ALDH+ cells in one human UPS.

FIGS. 33A-33C: MCA cells expressing CAS9 only (control) or CAS9+guide RNA for RALDH1 and RALDH3 (RALDH 1/3 double knockout) were transplanted and tumor volume (FIG. 33A), tumor weight (FIG. 33B), and Survival (FIG. 33C, based on maximum allowable tumor size) were measured. Tumor growth curve (FIG. 33A) or tumor weight (FIG. 33B) of RALDH1/3 DKO or Cas9 Control FS tumors implanted subcutaneously into C57BL/6 mice. Tumor volume was measured every three days starting at 7d post-implantation (n=8 tumors per group; data are representative of three independent experiments). FIG. 33C: Survival curve of mice bearing RALDH1/3 DKO or Cas9 Control FS tumors implanted subcutaneously in C57BL/6 mice (n=12 tumors per group; data are aggregated from three independent experiments). FIG. 33D: Control and double knockout MCA cells were transplanted, followed by treatment with anti-PD1 or control isotype antibodies as denoted. Anti-PD1 (or isotype control antibody) was administered to C57BL/6 mice starting 7d post-implantation of RALDH/3 DKO or Cas9 control tumors. Three doses (200 ug i.p.) at Day 7, 10 and 13 were given. Shown are the tumor growth curves. FIG. 33E: Non-modified parental MCA sarcoma cells were transplanted. After the tumors became detectable, mice were divided into two groups; those receiving anti-PD1 antibody and those receiving control isotype antibody, both via intra-peritoneal injection. Each group was further divided into two: intratumoral injection with the pan-RAR antagonist BMS493 and intratumoral injection with control DMSO. Tumor volume was measured over time. Each line represents an individual mouse. Individual growth curves of FS tumors treated with aPD1 (or isotype control) in combination with intratumoral BMS493 (or DMSO) are shown. (n=5 tumors per group).

DETAILED DESCRIPTION

Definitions

Figure 1:
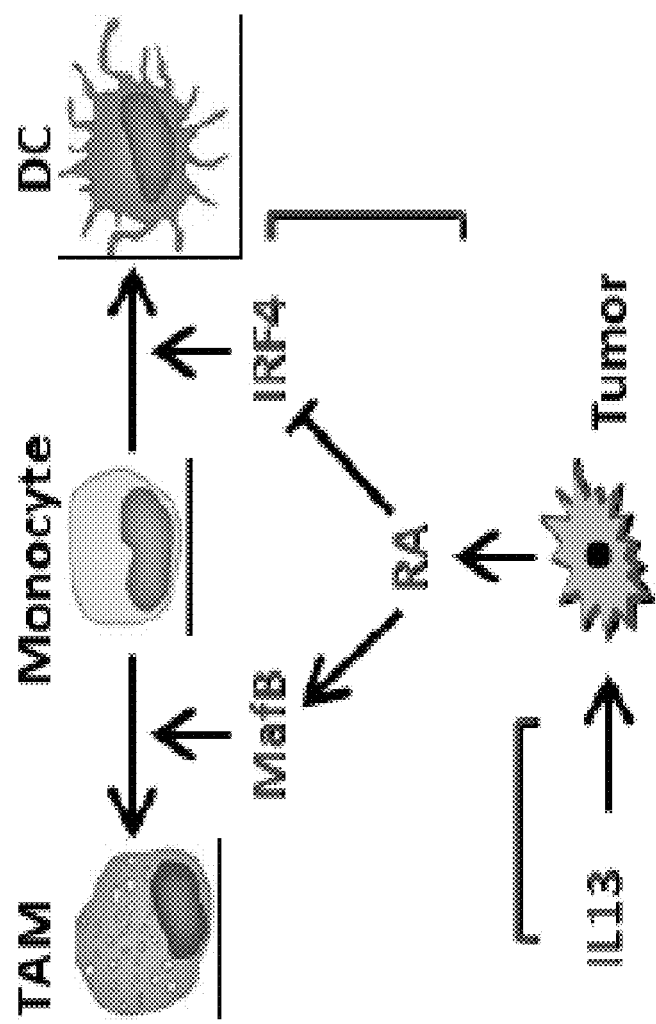
FIG. 1 is a schematic that illustrates the pathways for monocyte differentiation into tumor-associated macrophages (TAMs) or dendritic cells (DCs).

Unless defined otherwise, all technical and scientific terms used herein have the same meaning as commonly understood by one of ordinary skill in the art to which the invention pertains. Although any methods and materials similar or equivalent to those described herein can be used in the practice for testing of the present invention, the preferred materials and methods are described herein. In describing and claiming the present invention, the following terminology will be used.

It is also to be understood that the terminology used herein is for the purpose of describing particular embodiments only, and is not intended to be limiting.

The articles "a" and "an" are used herein to refer to one or to more than one (i.e., to at least one) of the grammatical object of the article. By way of example, "an element" means one element or more than one element.

"About" as used herein when referring to a measurable value such as an amount, a temporal duration, and the like, is meant to encompass variations of ±20% or ±10%, more preferably ±5%, even more preferably ±1%, and still more preferably ±0.1% from the specified value, as such variations are appropriate to perform the disclosed methods.

The term "anti-tumor effect" as used herein, refers to a biological effect which can be manifested by a decrease in tumor volume, a decrease in the number of tumor cells, a decrease in the number of metastases, an increase in life expectancy, or amelioration of various physiological symptoms associated with the cancerous condition. An "anti-tumor effect" can also be manifested by the ability of the peptides, polynucleotides, molecules, cells and antibodies of the invention in prevention of the occurrence of tumor in the first place.

The term "cancer" as used herein is defined as disease characterized by the rapid and uncontrolled growth of aberrant cells. Cancer cells can spread locally or through the bloodstream and lymphatic system to other parts of the body. Examples of various cancers include but are not limited to, breast cancer, prostate cancer, ovarian cancer, cervical cancer, skin cancer, pancreatic cancer, colorectal cancer, renal cancer, liver cancer, brain cancer, lymphoma, leukemia, lung cancer and the like. In certain embodiments, the cancer is medullary thyroid carcinoma.

The term "cleavage" refers to the breakage of covalent bonds, such as in the backbone of a nucleic acid molecule. Cleavage can be initiated by a variety of methods, including, but not limited to, enzymatic or chemical hydrolysis of a phosphodiester bond. Both single-stranded cleavage and double-stranded cleavage are possible. Double-stranded cleavage can occur as a result of two distinct single-stranded cleavage events. DNA cleavage can result in the production of either blunt ends or staggered ends. In certain embodiments, fusion polypeptides may be used for targeting cleaved double-stranded DNA.

The term "CRISPR/CAS," "clustered regularly inter-spaced short palindromic repeats system," or "CRISPR" refers to DNA loci containing short repetitions of base sequences. Each repetition is followed by short segments of spacer DNA from previous exposures to a virus. Bacteria and archaea have evolved adaptive immune defenses termed CRISPR-CRISPR-associated (Cas) systems that use short RNA to direct degradation of foreign nucleic acids. In bacteria, the CRISPR system provides acquired immunity against invading foreign DNA via RNA-guided DNA cleavage.

In the type II CRISPR/Cas system, short segments of foreign DNA, termed "spacers" are integrated within the CRISPR genomic loci and transcribed and processed into short CRISPR RNA (crRNA). These crRNAs anneal to trans-activating crRNAs (tracrRNAs) and direct sequence-specific cleavage and silencing of pathogenic DNA by Cas proteins. Recent work has shown that target recognition by the Cas9 protein requires a "seed" sequence within the crRNA and a conserved dinucleotide-containing protospacer adjacent motif (PAM) sequence upstream of the crRNA-binding region.

To direct Cas9 to cleave sequences of interest, crRNA-tracrRNA fusion transcripts, hereafter referred to as "guide RNAs" or "gRNAs" may be designed, from human U6 polymerase III promoter. CRISPR/CAS mediated genome editing and regulation, highlighted its transformative potential for basic science, cellular engineering and therapeutics.

The term "CRISPRi" refers to a CRISPR system for sequence specific gene repression or inhibition of gene expression, such as at the transcriptional level.

A "disease" is a state of health of an animal wherein the animal cannot maintain homeostasis, and wherein if the disease is not ameliorated then the animal's health continues to deteriorate. In contrast, a "disorder" in an animal is a state of health in which the animal is able to maintain homeostasis, but in which the animal's state of health is less favorable than it would be in the absence of the disorder. Left untreated, a disorder does not necessarily cause a further decrease in the animal's state of health.

"Effective amount" or "therapeutically effective amount" are used interchangeably herein, and refer to an amount of a compound, formulation, material, or composition, as described herein effective to achieve a particular biological result or provides a therapeutic or prophylactic benefit. Such results may include, but are not limited to, anti-tumor activity as determined by any means suitable in the art.

"Encoding" refers to the inherent property of specific sequences of nucleotides in a polynucleotide, such as a gene, a cDNA, or an mRNA, to serve as templates for synthesis of other polymers and macromolecules in biological processes having either a defined sequence of nucleotides (i.e., rRNA, tRNA and mRNA) or a defined sequence of amino acids and the biological properties resulting therefrom. Thus, a gene encodes a protein if transcription and translation of mRNA corresponding to that gene produces the protein in a cell or other biological system. Both the coding strand, the nucleotide sequence of which is identical to the mRNA sequence and is usually provided in sequence listings, and the non-coding strand, used as the template for transcription of a gene or cDNA, can be referred to as encoding the protein or other product of that gene or cDNA.

As used herein "endogenous" refers to any material from or produced inside an organism, cell, tissue or system.

As used herein, the term "exogenous" refers to any material introduced from or produced outside an organism, cell, tissue or system.

The term "expand" as used herein refers to increasing in number, as in an increase in the number of T cells. In one embodiment, the T cells that are expanded ex vivo increase in number relative to the number originally present in the culture. In another embodiment, the T cells that are expanded ex vivo increase in number relative to other cell types in the culture. The term "ex vivo," as used herein, refers to cells that have been removed from a living organism, (e.g., a human) and propagated outside the organism (e.g., in a culture dish, test tube, or bioreactor).

The term "expression" as used herein is defined as the transcription and/or translation of a particular nucleotide sequence driven by its promoter.

"Expression vector" refers to a vector comprising a recombinant polynucleotide comprising expression control sequences operatively linked to a nucleotide sequence to be expressed. An expression vector comprises sufficient cis-acting elements for expression; other elements for expression can be supplied by the host cell or in an in vitro expression system. Expression vectors include all those known in the art, such as cosmids, plasmids (e.g., naked or contained in liposomes) and viruses (e.g., sendai viruses, lentiviruses, retroviruses, adenoviruses, and adeno-associated viruses) that incorporate the recombinant polynucleotide.

"Homologous" as used herein, refers to the subunit sequence identity between two polymeric molecules, e.g., between two nucleic acid molecules, such as, two DNA molecules or two RNA molecules, or between two polypeptide molecules. When a subunit position in both of the two molecules is occupied by the same monomeric subunit; e.g., if a position in each of two DNA molecules is occupied by adenine, then they are homologous at that position. The homology between two sequences is a direct function of the number of matching or homologous positions; e.g., if half (e.g., five positions in a polymer ten subunits in length) of the positions in two sequences are homologous, the two sequences are 50% homologous; if 90% of the positions (e.g., 9 of 10), are matched or homologous, the two sequences are 90% homologous.

"Identity" as used herein refers to the subunit sequence identity between two polymeric molecules particularly between two amino acid molecules, such as, between two polypeptide molecules. When two amino acid sequences have the same residues at the same positions; e.g., if a position in each of two polypeptide molecules is occupied by an Arginine, then they are identical at that position. The identity or extent to which two amino acid sequences have the same residues at the same positions in an alignment is often expressed as a percentage. The identity between two amino acid sequences is a direct function of the number of matching or identical positions; e.g., if half (e.g., five positions in a polymer ten amino acids in length) of the positions in two sequences are identical, the two sequences are 50% identical; if 90% of the positions (e.g., 9 of 10), are matched or identical, the two amino acids sequences are 90% identical.

The term "immunoglobulin" or "Ig," as used herein is defined as a class of proteins, which function as antibodies. Antibodies expressed by B cells are sometimes referred to as the BCR (B cell receptor) or antigen receptor. The five members included in this class of proteins are IgA, IgG, IgM, IgD, and IgE. IgA is the primary antibody that is present in body secretions, such as saliva, tears, breast milk, gastrointestinal secretions and mucus secretions of the respiratory and genitourinary tracts. IgG is the most common circulating antibody. IgM is the main immunoglobulin produced in the primary immune response in most subjects. It is the most efficient immunoglobulin in agglutination, complement fixation, and other antibody responses, and is important in defense against bacteria and viruses. IgD is the immunoglobulin that has no known antibody function, but may serve as an antigen receptor. IgE is the immunoglobulin that mediates immediate hypersensitivity by causing release of mediators from mast cells and basophils upon exposure to allergen.

The term "immune response" as used herein is defined as a cellular response to an antigen that occurs when lymphocytes identify antigenic molecules as foreign and induce the formation of antibodies and/or activate lymphocytes to remove the antigen.

"Isolated" means altered or removed from the natural state. For example, a nucleic acid or a peptide naturally present in a living animal is not "isolated," but the same nucleic acid or peptide partially or completely separated from the coexisting materials of its natural state is "isolated." An isolated nucleic acid or protein can exist in substantially purified form, or can exist in a non-native environment such as, for example, a host cell.

By the term "modified" as used herein, is meant a changed state or structure of a molecule or cell of the invention. Molecules may be modified in many ways, including chemically, structurally, and functionally. Cells may be modified through the introduction of nucleic acids.

By the term "modulating," as used herein, is meant mediating a detectable increase or decrease in the level of a response in a subject compared with the level of a response in the subject in the absence of a treatment or compound, and/or compared with the level of a response in an otherwise identical but untreated subject. The term encompasses perturbing and/or affecting a native signal or response thereby mediating a beneficial therapeutic response in a subject, preferably, a human.

In the context of the present invention, the following abbreviations for the commonly occurring nucleic acid bases are used. "A" refers to adenosine, "C" refers to cytosine, "G" refers to guanosine, "T" refers to thymidine, and "U" refers to uridine.

Unless otherwise specified, a "nucleotide sequence encoding an amino acid sequence" includes all nucleotide sequences that are degenerate versions of each other and that encode the same amino acid sequence. The phrase nucleotide sequence that encodes a protein or an RNA may also include introns to the extent that the nucleotide sequence encoding the protein may in some version contain an intron(s).

The term "operably linked" refers to functional linkage between a regulatory sequence and a heterologous nucleic acid sequence resulting in expression of the latter. For example, a first nucleic acid sequence is operably linked with a second nucleic acid sequence when the first nucleic acid sequence is placed in a functional relationship with the second nucleic acid sequence. For instance, a promoter is operably linked to a coding sequence if the promoter affects the transcription or expression of the coding sequence. Generally, operably linked DNA sequences are contiguous and, where necessary to join two protein coding regions, in the same reading frame.

"Parenteral" administration of an immunogenic composition includes, e.g., subcutaneous (s.c.), intravenous (i.v.), intramuscular (i.m.), or intrasternal injection, or infusion techniques.

The term "polynucleotide" as used herein is defined as a chain of nucleotides. Furthermore, nucleic acids are polymers of nucleotides. Thus, nucleic acids and polynucleotides as used herein are interchangeable. One skilled in the art has the general knowledge that nucleic acids are polynucleotides, which can be hydrolyzed into the monomeric "nucleotides." The monomeric nucleotides can be hydrolyzed into nucleosides. As used herein polynucleotides include, but are not limited to, all nucleic acid sequences which are obtained by any means available in the art, including, without limitation, recombinant means, i.e., the cloning of nucleic acid sequences from a recombinant library or a cell genome, using ordinary cloning technology and PCR™, and the like, and by synthetic means.

As used herein, the terms "peptide," "polypeptide," and "protein" are used interchangeably, and refer to a compound comprised of amino acid residues covalently linked by peptide bonds. A protein or peptide must contain at least two amino acids, and no limitation is placed on the maximum number of amino acids that can comprise a protein's or peptide's sequence. Polypeptides include any peptide or protein comprising two or more amino acids joined to each other by peptide bonds. As used herein, the term refers to both short chains, which also commonly are referred to in the art as peptides, oligopeptides and oligomers, for example, and to longer chains, which generally are referred to in the art as proteins, of which there are many types. "Polypeptides" include, for example, biologically active fragments, substantially homologous polypeptides, oligopeptides, homodimers, heterodimers, variants of polypeptides, modified polypeptides, derivatives, analogs, fusion proteins, among others. The polypeptides include natural peptides, recombinant peptides, synthetic peptides, or a combination thereof.

The term "promoter" as used herein is defined as a DNA sequence recognized by the synthetic machinery of the cell, or introduced synthetic machinery, required to initiate the specific transcription of a polynucleotide sequence.

As used herein, the term "promoter/regulatory sequence" means a nucleic acid sequence which is required for expression of a gene product operably linked to the promoter/regulatory sequence. In some instances, this sequence may be the core promoter sequence and in other instances, this sequence may also include an enhancer sequence and other regulatory elements which are required for expression of the gene product. The promoter/regulatory sequence may, for example, be one which expresses the gene product in a tissue specific manner.

A "constitutive" promoter is a nucleotide sequence which, when operably linked with a polynucleotide which encodes or specifies a gene product, causes the gene product to be produced in a cell under most or all physiological conditions of the cell.

An "inducible" promoter is a nucleotide sequence which, when operably linked with a polynucleotide which encodes or specifies a gene product, causes the gene product to be produced in a cell substantially only when an inducer which corresponds to the promoter is present in the cell.

A "tissue-specific" promoter is a nucleotide sequence which, when operably linked with a polynucleotide encodes or specified by a gene, causes the gene product to be produced in a cell substantially only if the cell is a cell of the tissue type corresponding to the promoter.

By the term "specifically binds," as used herein with respect to an antibody, is meant an antibody which recognizes a specific antigen, but does not substantially recognize or bind other molecules in a sample. For example, an antibody that specifically binds to an antigen from one species may also bind to that antigen from one or more species. But, such cross-species reactivity does not itself alter the classification of an antibody as specific. In another example, an antibody that specifically binds to an antigen may also bind to different allelic forms of the antigen. However, such cross reactivity does not itself alter the classification of an antibody as specific. In some instances, the terms "specific binding" or "specifically binding," can be used in reference to the interaction of an antibody, a protein, or a peptide with a second chemical species, to mean that the interaction is dependent upon the presence of a particular structure (e.g., an antigenic determinant or epitope) on the chemical species; for example, an antibody recognizes and binds to a specific protein structure rather than to proteins generally. If an antibody is specific for epitope "A", the presence of a molecule containing epitope A (or free, unlabeled A), in a reaction containing labeled "A" and the antibody, will reduce the amount of labeled A bound to the antibody.

The term "subject" is intended to include living organisms in which an immune response can be elicited (e.g., mammals). A "subject" or "patient," as used therein, may be a human or non-human mammal. Non-human mammals include, for example, livestock and pets, such as ovine, bovine, porcine, canine, feline and murine mammals. Preferably, the subject is human.

As used herein, a "substantially purified" cell is a cell that is essentially free of other cell types. A substantially purified cell also refers to a cell which has been separated from other cell types with which it is normally associated in its naturally occurring state. In some instances, a population of substantially purified cells refers to a homogenous population of cells. In other instances, this term refers simply to cell that have been separated from the cells with which they are naturally associated in their natural state. In some embodiments, the cells are cultured in vitro. In other embodiments, the cells are not cultured in vitro.

A "target site" or "target sequence" refers to a genomic nucleic acid sequence that defines a portion of a nucleic acid to which a binding molecule may specifically bind under conditions sufficient for binding to occur.

The term "therapeutic" as used herein means a treatment and/or prophylaxis. A therapeutic effect is obtained by suppression, remission, or eradication of a disease state.

The term "transfected" or "transformed" or "transduced" as used herein refers to a process by which exogenous nucleic acid is transferred or introduced into the host cell. A "transfected" or "transformed" or "transduced" cell is one which has been transfected, transformed or transduced with exogenous nucleic acid. The cell includes the primary subject cell and its progeny.

To "treat" a disease as the term is used herein, means to reduce the frequency or severity of at least one sign or symptom of a disease or disorder experienced by a subject.

The phrase "under transcriptional control" or "operatively linked" as used herein means that the promoter is in the correct location and orientation in relation to a polynucleotide to control the initiation of transcription by RNA polymerase and expression of the polynucleotide.

A "vector" is a composition of matter which comprises an isolated nucleic acid and which can be used to deliver the isolated nucleic acid to the interior of a cell. Numerous vectors are known in the art including, but not limited to, linear polynucleotides, polynucleotides associated with ionic or amphiphilic compounds, plasmids, and viruses. Thus, the term "vector" includes an autonomously replicating plasmid or a virus. The term should also be construed to include non-plasmid and non-viral compounds which facilitate transfer of nucleic acid into cells, such as, for example, polylysine compounds, liposomes, and the like. Examples of viral vectors include, but are not limited to, Sendai viral vectors, adenoviral vectors, adeno-associated virus vectors, retroviral vectors, lentiviral vectors, and the like.

Ranges: throughout this disclosure, various aspects of the invention can be presented in a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 2.7, 3, 4, 5, 5.3, and 6. This applies regardless of the breadth of the range.

Description

Figure 2:
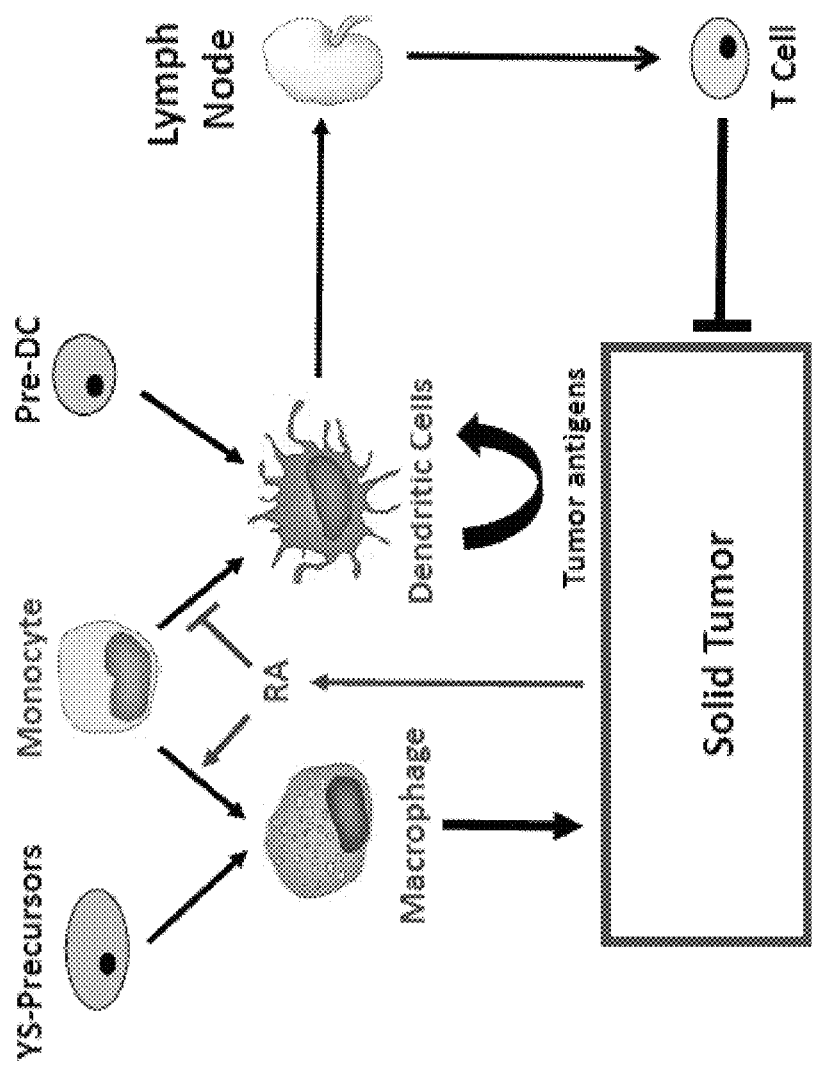
FIG. 2 is a schematic that illustrates the discovery by the present inventors that tumors produce large amounts of retinoic acid (RA), which blocks monocyte differentiation into DCs, instead generating TAMs. It was discovered that blocking RA production by the tumor cells or blocking RA signaling in the tumor-infiltrating monocytes increased the frequency of immunostimulatory DCs while reducing TAMs in a mouse model of fibrosarcoma. Importantly, RA-blockade dramatically synergized with anti-PD1 therapy to induce long-term remission in these mouse models. Therefore, RA signaling blockade, alone or in combination with immune checkpoint blockade, is a novel approach in solid tumor immunotherapy.
Figure 3:
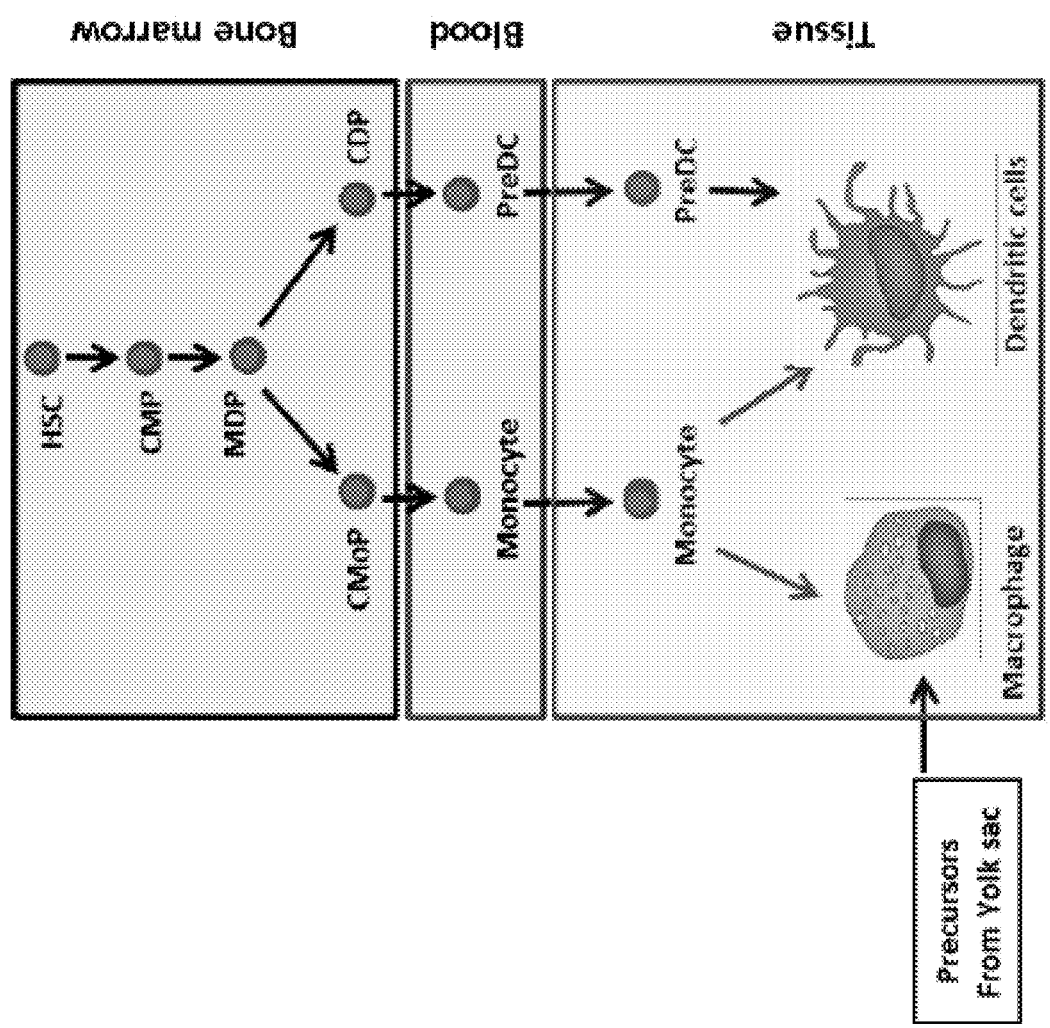
FIG. 3 is a schematic that illustrates the ontogeny of mononuclear phagocytes. The figures is a schematic of macrophage, monocyte and dendritic cell development. HSC: Hematopoietic stem cells, CMP: Common myeloid progenitor, MDP: Macrophage DC progenitor, CMoP: Common monocyte progenitor, PreDC. Pre-dendritic cells. Macrophage and DCs depicted here represent all subsets. Yok sac-derived progenitors of macrophages seed tissue during embryogenesis and are maintained by proliferation.

The present inventors discovered that tumors produce large amounts of retinoic acid (RA), which blocks monocyte differentiation into DCs, instead generating TAMs, as illustrated in FIG. 2. DCs are key are key cells of the immune system that (1) detect infection or cancer, (2) alert the rest of the immune system, (3) initiate appropriate T cell responses, and (4) provide support to the activated T cells. Without DCs, there cannot be a productive adaptive immune response. Macrophages are closely related to DCs, but within tumors (TAMs) they are generally immunosuppressive and help promote tumor growth. Macrophages and DCs can originate from monocytes or other precursor cells. However, monocytes are far more abundant than DC precursors (Pre-DC). Most solid tumors have abundant monocyte-derived TAMs but rare DCs. The reason why monocytes generate TAMs but not DCs was not previously understood.

It was discovered by the present inventors that blocking RA production by the tumor cells or blocking RA signaling in the tumor-infiltrating monocytes increased the frequency of immunostimulatory DCs while reducing TAMs in a mouse model of fibrosarcoma. Importantly, RA-blockade dramatically synergized with anti-PD1 therapy to induce long-term remission in these mouse models. Therefore, blocking RA signaling, for example through the use of a retinoic acid receptor inhibitor, a retinoic X receptor inhibitor, or an inhibitor of an enzyme in the retinoic acid biosynthesis pathway, alone or in combination with immune checkpoint blockade, is a novel approach in solid tumor immunotherapy.

Provided is a method for treating a patient having a solid tumor, the method comprising administering to the patient an effective amount of a retinoic acid receptor inhibitor, a retinoic X receptor inhibitor, or any combination thereof. In some embodiments, the method further comprising administering to the patient an immune checkpoint inhibitor. In some embodiments, the method further comprises administering to the patient an anti-IL13 antibody or fragment thereof.

Provided is a composition comprising: a retinoic acid receptor inhibitor, a retinoic X receptor inhibitor or any combination thereof; and an immune checkpoint inhibitor.

In some embodiments, the composition further comprises an anti-IL13 antibody.

Provided is a method for treating a patient having a solid tumor, the method comprising administering to the patient an effective amount of an inhibitor of an enzyme in the retinoic acid biosynthesis pathway. In some embodiments, the method further comprising administering to the patient an immune checkpoint inhibitor. In some embodiments, the method further comprises administering to the patient an anti-IL13 antibody or fragment thereof.

Provided is a composition comprising an inhibitor of an enzyme in the retinoic acid biosynthesis pathway and an immune checkpoint inhibitor. In some embodiments, the composition further comprises an anti-IL13 antibody.

Provided is a method of selecting a patient having a solid tumor for treatment with a retinoic acid receptor inhibitor, a retinoic X receptor inhibitor or an inhibitor of an enzyme in the retinoic acid biosynthesis pathway. The method comprises obtaining a tumor sample from a patient; detecting the expression level of a retinoic acid regulated gene in the tumor sample; and selecting the patient for treatment with a retinoic acid receptor inhibitor, a retinoic X receptor inhibitor or an inhibitor of an enzyme in the retinoic acid biosynthesis pathway if the expression level of the retinoic acid regulated gene is above that of a control.

In some embodiments, the solid tumor is a sarcoma, lymphoma, carcinoma or melanoma. In further embodiments, the solid tumor is a sarcoma. In some embodiments, the sarcoma is Kaposi's sarcoma, gynecologic sarcoma, uterus sarcoma, soft tissue sarcoma, or leiomyosarcoma, synovial sarcoma (SS), undifferentiated pleomorphic sarcoma (UPS), or fibrosarcoma.

In some embodiments, the carcinoma is a mammary ductal carcinoma, lobular carcinoma, adenocarcinoma (e.g. pancreatic cancer or colon cancer), small cell lung carcinoma, non small cell lung carcinoma.

Retinoic Acid Receptor Inhibitor or Retinoic X Receptor Inhibitor

Retinoic acid receptor inhibitors or retinoic X receptor inhibitors for use in the methods described herein may be chemically synthesized by methods known in the art, or they may be purchased from commercial sources. In some embodiments, the retinoic acid receptor inhibitor is selected from the group consisting of AGN 193109, BMS 195614, BMS 493 CD 2665, ER 50891, LE 135, LY 2955303, MM 11253 any salt or solvate thereof, and any combinations thereof. AGN 193109 is a PAN-RAR antagonist. BMS 195614 is a selective RAR-alpha antagonist. BMS 493 is a PAN-RAR antagonist/inverse agonist. CD 2665 is a selective RAR-beta and RAR-gamma antagonist. ER 50891 is a selective RAR-alpha antagonist. LE 135 is a selective RAR-beta antagonist. LY 2955303 is a selective RAR-gamma antagonist. MM 11253 is a selective RAR-gamma antagonist.

In some embodiments, the retinoic X receptor inhibitor is selected from the group consisting of HX 531, PA 452, and UVI 3003, any salt or solvate thereof, and any combinations thereof. HX 531 is a PAN-RXR antagonist. PA 452 is a PAN-RXR antagonist. UVI 3003 is a PAN-RXR antagonist.

Inhibitors of an Enzyme in the Retinoic Acid Biosynthesis Pathway

Inhibitors of an enzyme in the retinoic acid biosynthesis pathway for use in the methods described herein may be chemically synthesized by methods known in the art, or they may be purchased from commercial sources. In some embodiments, inhibitors of retinaldehyde dehydrogenases to block retinoic acid biosynthesis is selected from the group consisting of Ampal, Benomyl, Citral, Chloral hydrate, chlorpropamide analog NPI-1, Coprine, Cyanamide, Daidzin, CVT-10216, DEAB, DPAB, Disulfiram, Gossypol, Molinate, Nitroglycerin, Pargyline, any salt or solvate thereof, and any combinations thereof.

Immune Checkpoint Inhibitor

In some embodiments, an immune checkpoint inhibitor is administered to the patient. In some embodiments, the immune checkpoint inhibitor is selected from the group consisting of an anti-PD1 antibody, an anti-PD-L1, an anti-CTLA4 antibody, any fragment thereof, and any combinations thereof. In some embodiments, the anti-PD1 antibody is lambrolizumab. In some embodiments, the immune checkpoint inhibitor is an antibody that blocks the interaction between the PD1 receptor and its ligands PD-L1 and PD-L2.

Pharmaceutical Compositions

Pharmaceutical compositions of the present invention may comprise a retinoic acid pathway inhibitor as described herein, and/or an immune checkpoint inhibitor, in combination with one or more pharmaceutically or physiologically acceptable carriers, diluents, adjuvants or excipients. Such compositions may comprise buffers such as neutral buffered saline, phosphate buffered saline and the like; carbohydrates such as glucose, mannose, sucrose or dextrans, mannitol; proteins; polypeptides or amino acids such as glycine; antioxidants; chelating agents such as EDTA or glutathione; adjuvants (e.g., aluminum hydroxide); and preservatives. Compositions of the present invention are preferably formulated for intravenous administration.

Pharmaceutical compositions of the present invention may be administered in a manner appropriate to the disease to be treated (or prevented). The quantity and frequency of administration will be determined by such factors as the condition of the patient, and the type and severity of the patient's disease, although appropriate dosages may be determined by clinical trials.

The dosage of the above treatments to be administered to a patient will vary with the precise nature of the condition being treated and the recipient of the treatment. The scaling of dosages for human administration can be performed according to art-accepted practices. The dose for CAMPATH, for example, will generally be in the range 1 to about 100 mg for an adult patient, usually administered daily for a period between 1 and 30 days. The preferred daily dose is 1 to 10 mg per day although in some instances larger doses of up to 40 mg per day may be used (described in U.S. Pat. No. 6,120,766).

The dosage of an inhibitor, for example a retinoic acid receptor inhibitor or a retinoic X receptor inhibitor or an inhibitor of an enzyme in the retinoic acid biosynthesis pathway, to be administered to a patient may be from about 0.1 to about 100 mg/m$^2$. In certain embodiments, the dosage may be from about 0.1 to about 70 mg/m$^2$. In certain embodiments, the dosage may be from about 0.1 to about 60 mg/m$^2$. In some embodiments, the dosage may be from about 0.1 to about 1, 5, 10, 15, 20, 15, 30, 35, 40, 41, 42, 43, 44, 45, 46, 47, 48, 49, 50, 51, 52, 53, 54, 55, 56, 57, 58, 59 or 60 mg/m$^2$. In some embodiments, the dosage may be about 0.1, 1, 5, 10, 15, 20, 15, 30, 35, 40, 41, 42, 43, 44, 45, 46, 47, 48, 49, 50, 51, 52, 53, 54, 55, 56, 57, 58, 59 or 60 mg/m$^2$.

Human dosage amounts can initially be determined by extrapolating from the amount of compound used in mice, as a skilled artisan recognizes it is routine in the art to modify the dosage for humans compared to animal models. In certain embodiments it is envisioned that the dosage may include an effective amount from between about 0.001 mg compound/Kg body weight to about 100 mg compound/Kg body weight; or from about 0.05 mg/Kg body weight to about 75 mg/Kg body weight or from about 0.1 mg/Kg body weight to about 50 mg/Kg body weight; or from about 0.5 mg/Kg body weight to about 40 mg/Kg body weight; or from about 0.1 mg/Kg body weight to about 30 mg/Kg body weight; or from about 1 mg/Kg body weight to about 20 mg/Kg body weight. In other embodiments, the effective amount may be about 0.001, 0.002, 0.003, 0.004, 0.005, 0.006, 0.007, 0.008, 0.009, 0.01, 0.02, 0.03, 0.04, 0.05, 0.06, 0.07, 0.08, 0.09, 0.1, 0.2, 0.3, 0.4, 0.5, 0.6, 0.7, 0.8, 0.9, 1, 2, 3, 4, 5, 6, 7, 8, 9, 10, 15, 20, 25, 30, 35, 40, 45, 50, 55, 60, 65, 70, 75, 80, 85, 90, 95, or about 100 mg/Kg body weight. In other embodiments, it is envisaged that effective amounts may be in the range of about 2 mg compound to about 100 mg compound. In other embodiments, the effective amount may be about 1, 2, 3, 4, 5, 6, 7, 8, 9, 10, 11, 12, 13, 14, 15, 16, 17, 18, 19, or 20 mg per single dose. In another embodiment, the effective amount comprises less than about 2, 3, 4, 5, 6, 7, 8, 9, 10, 15, 20, 25, 30, 35, 40, 45, 50, 55, 60, 65, 70, 75, 80, 85, 90, 95 mg daily. In an exemplary embodiment, the effective amount comprises less than about 50 mg daily. Of course, the single dosage amount or daily dosage amount may be adjusted upward or downward, as is routinely done in such treatment protocols, depending on the results of the initial clinical trials and the needs of a particular patient.

The precise determination of what would be considered an effective dose is based on factors individual to each subject, including their size, age, sex, weight, and condition of the particular subject. Dosages can be readily ascertained by those skilled in the art from this disclosure and the knowledge in the art.

Optionally, the methods of the invention provide for the administration of a composition of the invention to a suitable animal model to identify the dosage of the composition(s), concentration of components therein and timing of administering the composition(s), which elicit tissue repair, reduce cell death, or induce another desirable biological response. Such determinations do not require undue experimentation, but are routine and can be ascertained without undue experimentation.

The biologically active agents can be conveniently provided to a subject as sterile liquid preparations, e.g., isotonic aqueous solutions, suspensions, emulsions, dispersions, or viscous compositions, which may be buffered to a selected pH. Cells and agents of the invention may be provided as liquid or viscous formulations. For some applications, liquid formations are desirable because they are convenient to administer, especially by injection. Where prolonged contact with a tissue is desired, a viscous composition may be preferred. Such compositions are formulated within the appropriate viscosity range. Liquid or viscous compositions can comprise carriers, which can be a solvent or dispersing medium containing, for example, water, saline, phosphate buffered saline, polyol (for example, glycerol, propylene glycol, liquid polyethylene glycol, and the like) and suitable mixtures thereof.

Sterile injectable solutions are prepared by suspending talampanel and/or perampanel in the required amount of the appropriate solvent with various amounts of the other ingredients, as desired. Such compositions may be in admixture with a suitable carrier, diluent, or excipient, such as sterile water, physiological saline, glucose, dextrose, or the like. The compositions can also be lyophilized. The compositions can contain auxiliary substances such as wetting, dispersing, or emulsifying agents (e.g., methylcellulose), pH buffering agents, gelling or viscosity enhancing additives, preservatives, flavoring agents, colors, and the like, depending upon the route of administration and the preparation desired. Standard texts, such as "REMINGTON'S PHARMACEUTICAL SCIENCE", 17th edition, 1985, incorporated herein by reference, may be consulted to prepare suitable preparations, without undue experimentation.

Various additives which enhance the stability and sterility of the compositions, including antimicrobial preservatives, antioxidants, chelating agents, and buffers, can be added. Prevention of the action of microorganisms can be ensured by various antibacterial and antifungal agents, for example, parabens, chlorobutanol, phenol, sorbic acid, and the like. Prolonged absorption of the injectable pharmaceutical form can be brought about by the use of agents delaying absorption, for example, aluminum monostearate and gelatin. According to the present invention, however, any vehicle, diluent, or additive used would have to be compatible with the cells or agents present in their conditioned media.

The compositions can be isotonic, i.e., they can have the same osmotic pressure as blood and lacrimal fluid. The desired isotonicity of the compositions of this invention may be accomplished using sodium chloride, or other pharmaceutically acceptable agents such as dextrose, boric acid, sodium tartrate, propylene glycol or other inorganic or organic solutes. Sodium chloride is preferred particularly for buffers containing sodium ions.

Viscosity of the compositions, if desired, can be maintained at the selected level using a pharmaceutically acceptable thickening agent, such as methylcellulose. Other suitable thickening agents include, for example, xanthan gum, carboxymethyl cellulose, hydroxypropyl cellulose, carbomer, and the like. The choice of suitable carriers and other additives will depend on the exact route of administration and the nature of the particular dosage form, e.g., liquid dosage form (e.g., whether the composition is to be formulated into a solution, a suspension, gel or another liquid form, such as a time release form or liquid-filled form). Those skilled in the art will recognize that the components of the compositions should be selected to be chemically inert.

It should be understood that the method and compositions that would be useful in the present invention are not limited to the particular formulations set forth in the examples. The following examples are put forth so as to provide those of ordinary skill in the art with a complete disclosure and description of how to make and use the cells, expansion and culture methods, and therapeutic methods of the invention, and are not intended to limit the scope of what the inventors regard as their invention.

The practice of the present invention employs, unless otherwise indicated, conventional techniques of molecular biology (including recombinant techniques), microbiology, cell biology, biochemistry and immunology, which are well within the purview of the skilled artisan. Such techniques are explained fully in the literature, such as, "Molecular Cloning: A Laboratory Manual", fourth edition (Sambrook, 2012); "Oligonucleotide Synthesis" (Gait, 1984); "Culture of Animal Cells" (Freshney, 2010); "Methods in Enzymology" "Handbook of Experimental Immunology" (Weir, 1997); "Gene Transfer Vectors for Mammalian Cells" (Miller and Calos, 1987); "Short Protocols in Molecular Biology" (Ausubel, 2002); "Polymerase Chain Reaction: Principles, Applications and Troubleshooting", (Babar, 2011); "Current Protocols in Immunology" (Coligan, 2002). These techniques are applicable to the production of the polynucleotides and polypeptides of the invention, and, as such, may be considered in making and practicing the invention. Particularly useful techniques for particular embodiments will be discussed in the sections that follow.

Experimental Examples

The invention is further described in detail by reference to the following experimental examples. These examples are provided for purposes of illustration only, and are not intended to be limiting unless otherwise specified. Thus, the invention should in no way be construed as being limited to the following examples, but rather, should be construed to encompass any and all variations which become evident as a result of the teaching provided herein.

Without further description, it is believed that one of ordinary skill in the art can, using the preceding description and the following illustrative examples, make and utilize the compounds of the present invention and practice the claimed methods. The following working examples therefore, specifically point out the preferred embodiments of the present invention, and are not to be construed as limiting in any way the remainder of the disclosure.

Sarcoma is a rare but heterogeneous collection of fatal malignancies that arise from mesenchymal tissue such as fat, muscle, cartilage, etc. Recent efforts to utilize immunotherapies such as immune checkpoint blockade in sarcoma have demonstrated efficacy only in a small percentage of patients, underscoring the importance of elucidating additional immune evasion mechanisms. Immunosuppressive tumor associated macrophages (TAMs) are abundant in the solid tumor microenvironment (TME) and pose a major barrier to effective anti-tumor immunity. Though circulating monocytes are a major reservoir for TAMs, how the TME governs intratumoral monocyte differentiation is poorly understood. In multiple types of mouse and human sarcoma, the present inventors found that the TME induced tumor cells to produce high levels of the tissue metabolite retinoic acid (RA). RA promoted intratumoral monocytes to differentiate into immunosuppressive TAMs and inhibited monocyte differentiation into dendritic cells. Sarcomas genetically modified to produce limited RA harbored a more stimulatory myeloid compartment and enhanced T cell dependent anti-tumor immunity. Notably, RA inhibition demonstrated robust synergy with immune checkpoint blockade therapy. Without wishing to be bound by theory, the present results suggest that RA is a local tissue metabolite that promotes myeloid-mediated immune suppression in sarcoma.

Example 1-Sarcomas Harbor Abundant TAMs and Rare DCs

The distribution, development, and function of APCs in solid tumors were studied using sarcomas as a model. Sarcomas are very heterogeneous with more than 60 diagnostic subtypes that can be loosely classified into three groups based on the underlying genetic aberrations: (1) sarcomas with unique translocation that create fusion oncogenes, (2) sarcomas with mutations in tumor suppressors or oncogenes, and (3) sarcomas with genomic instability but not demonstrating a consistent mutation. One mouse model representing each of the three groups was selected: (1) SYT-SSX fusion oncogene-driven mouse model of synovial sarcoma (SS) (Barrott et al. Oncotarget 6:22758-22766 (2015)), (2) undifferentiated pleomorphic sarcoma (UPS) induced by the loss of P53 and activation of KRAS (Kirsch et al. Nat. Med. 13:992-997 (2007)), and (3) fibrosarcoma generated by syngeneic subcutaneous transplant of tumor cells derived from methylcholanthrene-induced murine fibrosarcomas (MCA-sarcoma or MCAS) (Gubin et al. Nature 515:577-581 (2014)). SS was generated in mice conditionally expressing human SYT-SSX2 fusion oncogene and a stabilized form of β-catenin by injecting Cre protein (TAT-CRE, Millipore) in the hind limb musculature of Rosasyt-ssx:Catnblox(e3) mice. UPS was generated by hind limb intramuscular injection of TAT-Cre in KrasG12D: Trp53flox mice. Previous genomic profiling of tumors from the aforementioned models demonstrated (1) thousands of mutations in MCAS, (2) about 100-200 in UPS, and (3) a few dozen in SS. Therefore, besides representing the diversity of sarcomas the three mouse models also capture the range of mutational load associated with solid tumors in general.

Figures 6A, 6B:
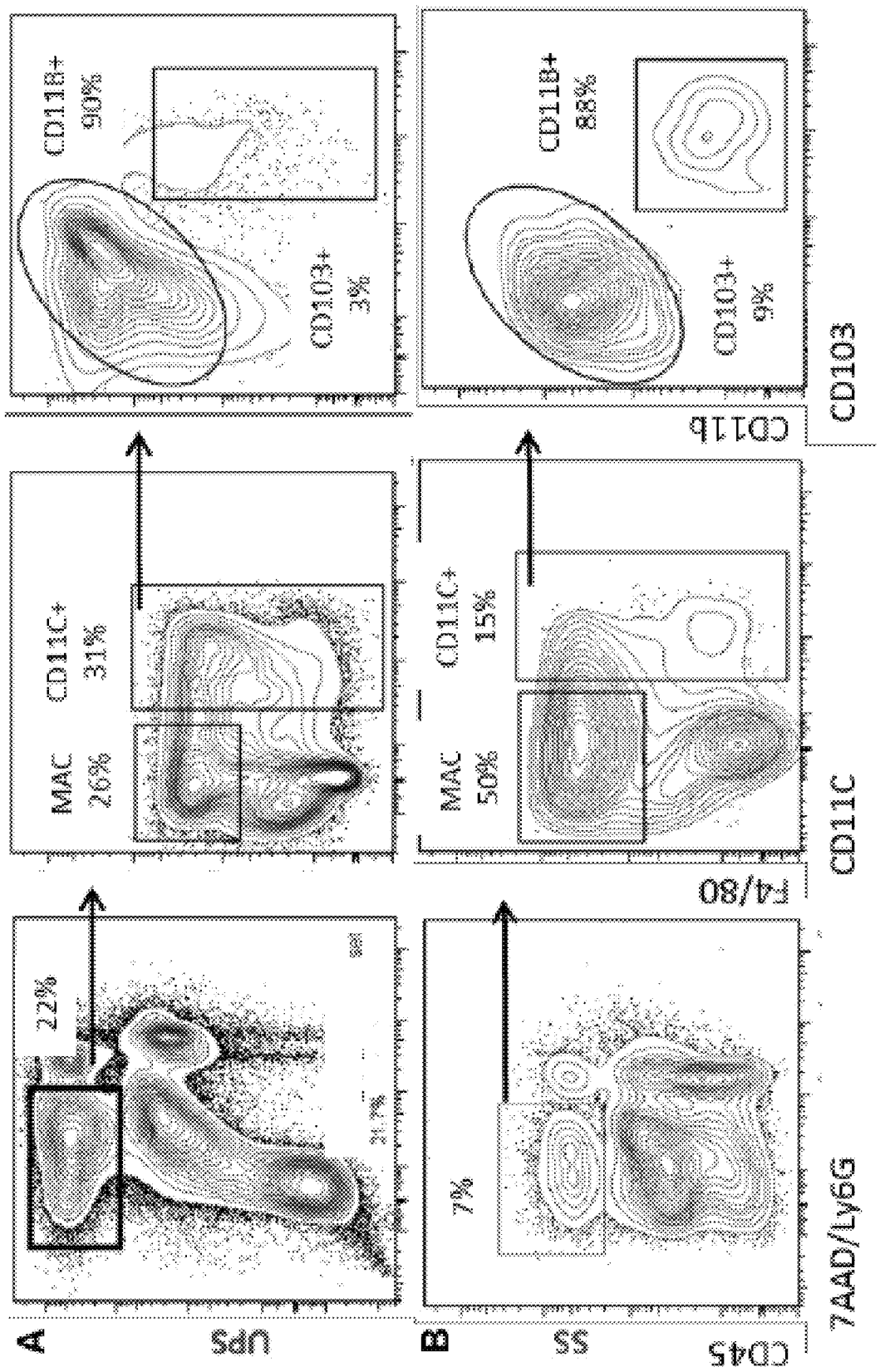
FIGS. 6A-6D illustrate APC distribution in sarcoma. UPS (FIG. 6A) and SS (FIG. 6B) tumors were dissociated into single cell suspension using Miltenyi gentleMACS™ octo dissociator, stained with indicated antibodies, and analyzed by FCM. Headers denote gating for the population shown below.
Figures 6C, 6D:
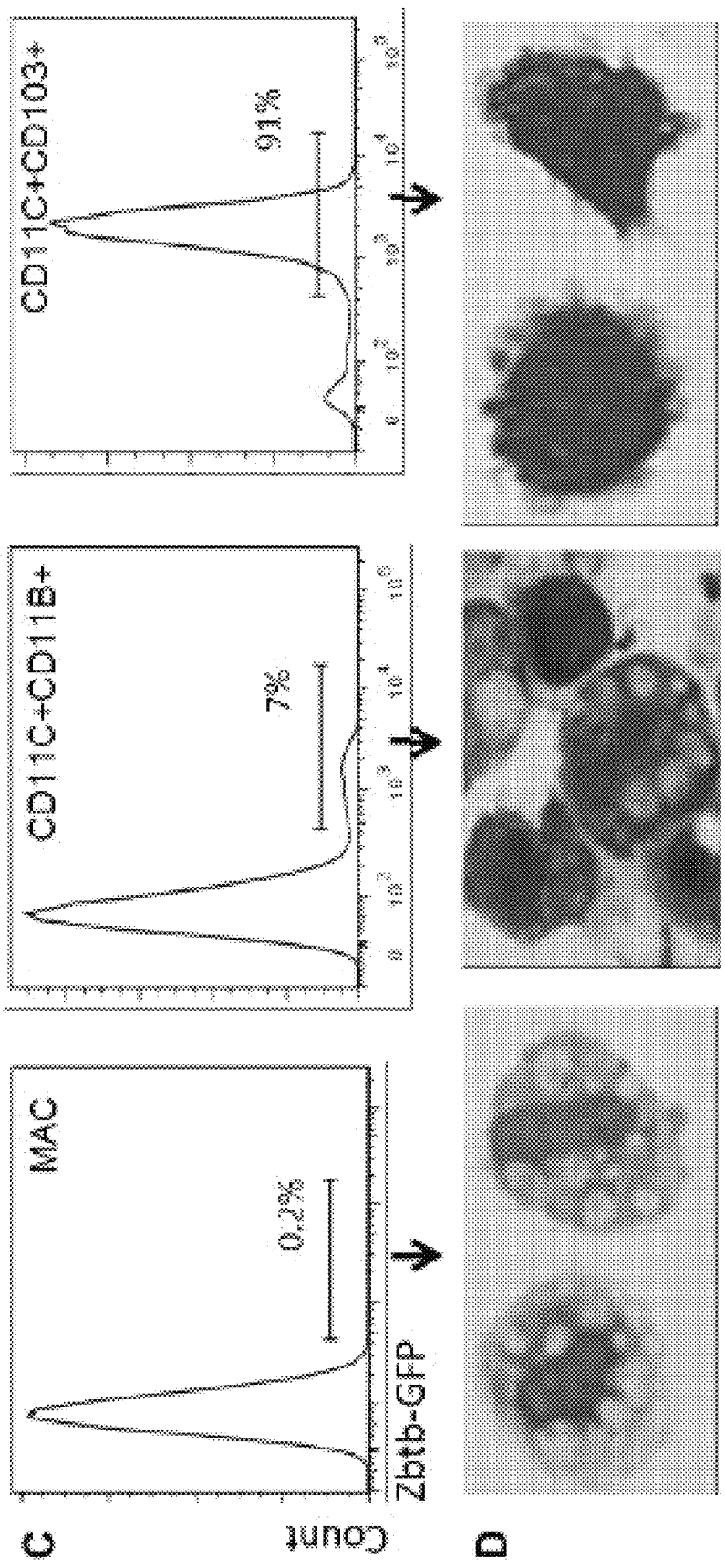

Intra-tumoral APCs were identified by the expression pattern of conventional APC surface markers in combination with the DC lineage reporter Zbtb46-GFP (FIGS. 6A-6C). To further confirm identity, each population was purified by FACS and their gene expression profile (microarray-based) compared to tissue APCs. In all three murine sarcoma models, F4/80+CD11C-macrophages were abundant (FIGS. 6A-6B). The F4/80+/−CD11C+MHCII+cells comprised of rare Zbtb46+DCs and numerous Zbtb46 negative cells (FIG. 6C). The majority of these Zbtb46 negative cells appear to be macrophages by morphology (FIG. 6D) and microarray-based gene expression profiling. Notably, GFP expression in Zbtb46-GFP reporter mice was key to distinguishing DCs from MACs in the mixed CD1C+MHCII+CD11B+population (FIG. 4C). There are two major subsets of tissue DCs distinguished by cell surface markers CD11b and CD10314. Both CD11b+CD103- and CD11b-CD103+subsets were detected in tumors from all three models (FIGS. 6A-6C).

Example 2-Monocytes Generate TAMs and CD11b+DCs in TME

Figures 7A, 7B:
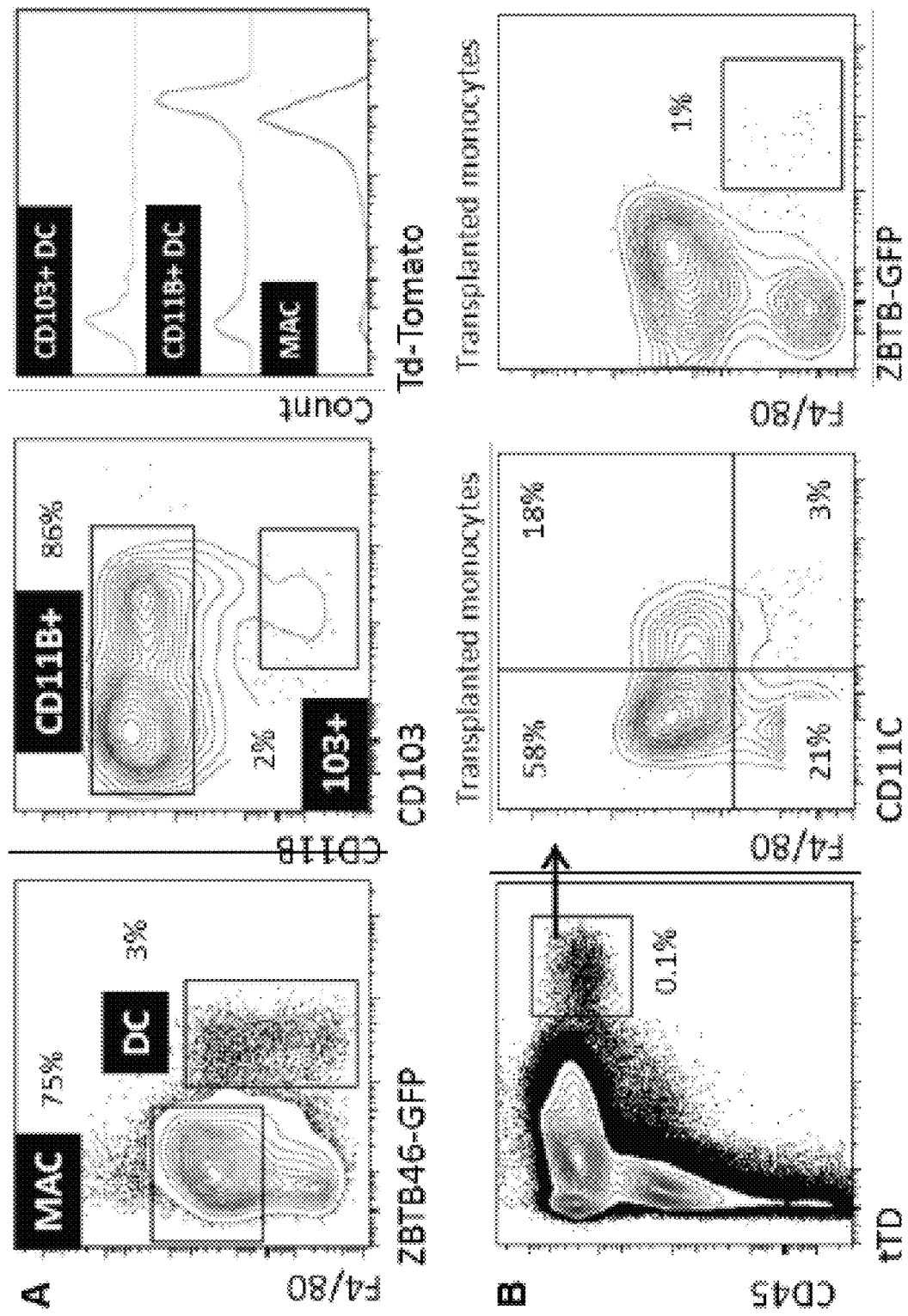
FIGS. 7A-7B illustrate the origin of sarcoma APCs.

To determine the origin of TAMs and DCs in TME, lineage-tracing studies were performed. LysmCre:RosatdT:Zbtb46GFP mice were generated that harbor Lysm-Cre (expresses Cre recombinase in monocytesxClausen et al. Transgenic Res. 8:256-277 (1999)), Rosa-TdTomato (expresses the fluorescent TdTomato in Cre-dependent manner) (Madisen et al. Nat. Neurosci. 13:133-140 (2010)), and Zbtb46-GFP (expresses GFP in DCs)(Satpathy et al. J. Exp. Med. 209:1135-1152 (2012)). These mice were transplanted with MCAS cells. Analyses of the resulting tumors revealed that the F4/80+TAMs and CD11b+DCs, but not CD103+ DCs, largely originated from monocytes (FIG. 7A). Intratumoral TAMs and CD11b+DCs were also reduced in CCR2 knockout (engenders monocyte deficiency) 50 mice; further confirming their monocyte origins. Finally, the ability of monocytes to differentiate into TAMs and DCs in situ within TME was confirmed by performing intra-tumoral monocyte transplant. Here, monocytes from LysmCre:RosatdT:Zbtb46GFP mice were injected into syngeneic MCAS fibrosarcomas. The fate of these monocytes was analyzed at various time points after transplantation using tdTomato expression to identify donor monocyte-derived cells. The results clearly demonstrate the propensity of monocytes to differentiate into TAMs but not DCs within TME (FIG. 7B).

Example 3-RA Blocks DC but Promotes TAM Differentiation from Monocytes

Figures 8A, 8B, 8C, 8D:
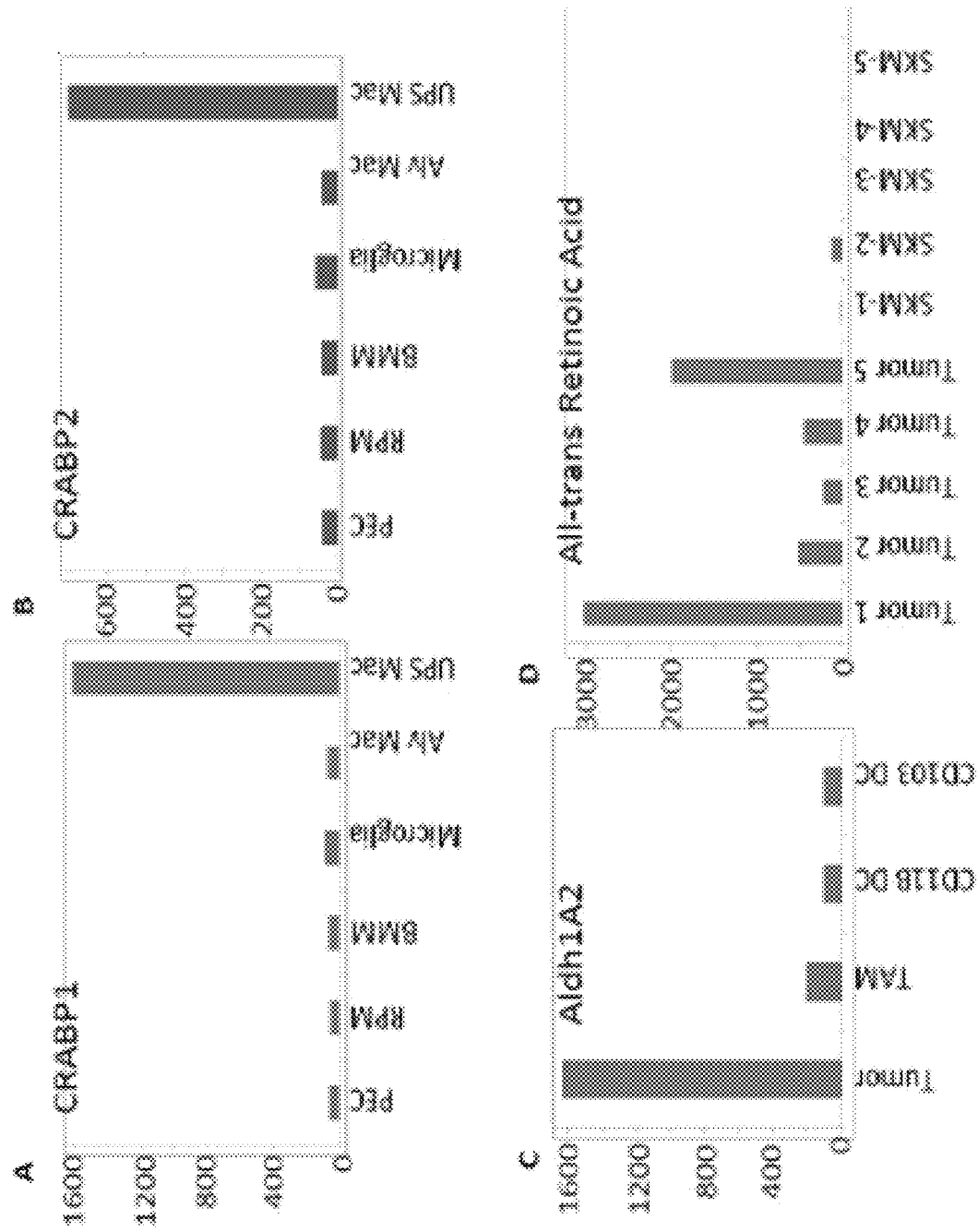
FIGS. 8A-8D illustrate RA activity in tumors.
Figure 9:
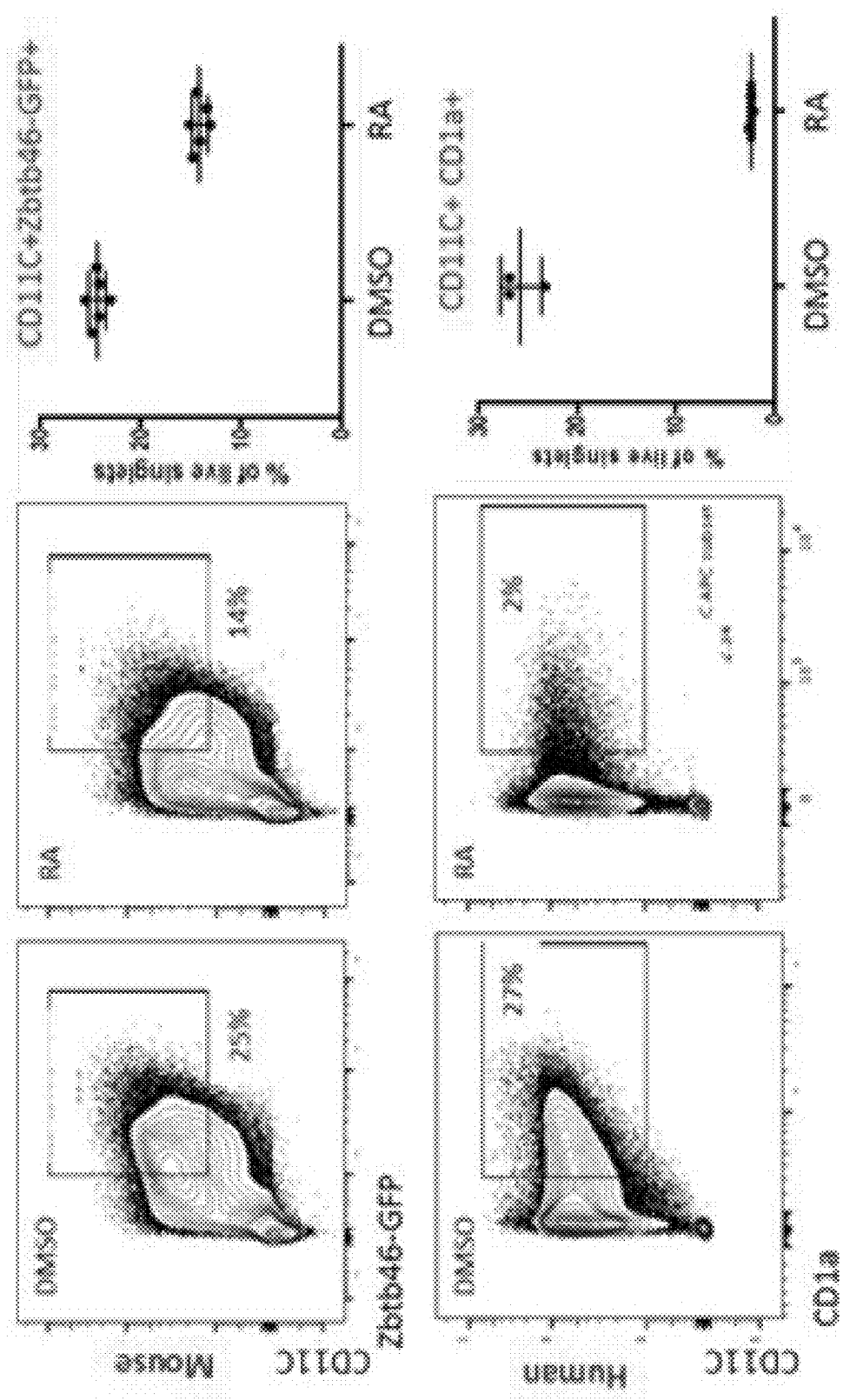
FIG. 9 illustrates that RA blocks monocyte-derived DCs. Mouse (top) and human (bottom) monocytes were cultured for 5 days in RPMI media containing 10% FCS and 20 ng/ml (mouse) or 50 ng/ml (human) of GM-CSF and IL4. RA (100 nM mice 20 nM human) or DMSO were added at the onset of culture and cells analyzed by FCM after five days. The plots on right quantify the differences in population defined by the indicated markers ($P<0.01$, N=3 per experiment, and >5 experiments).
Figures 10A, 10B:
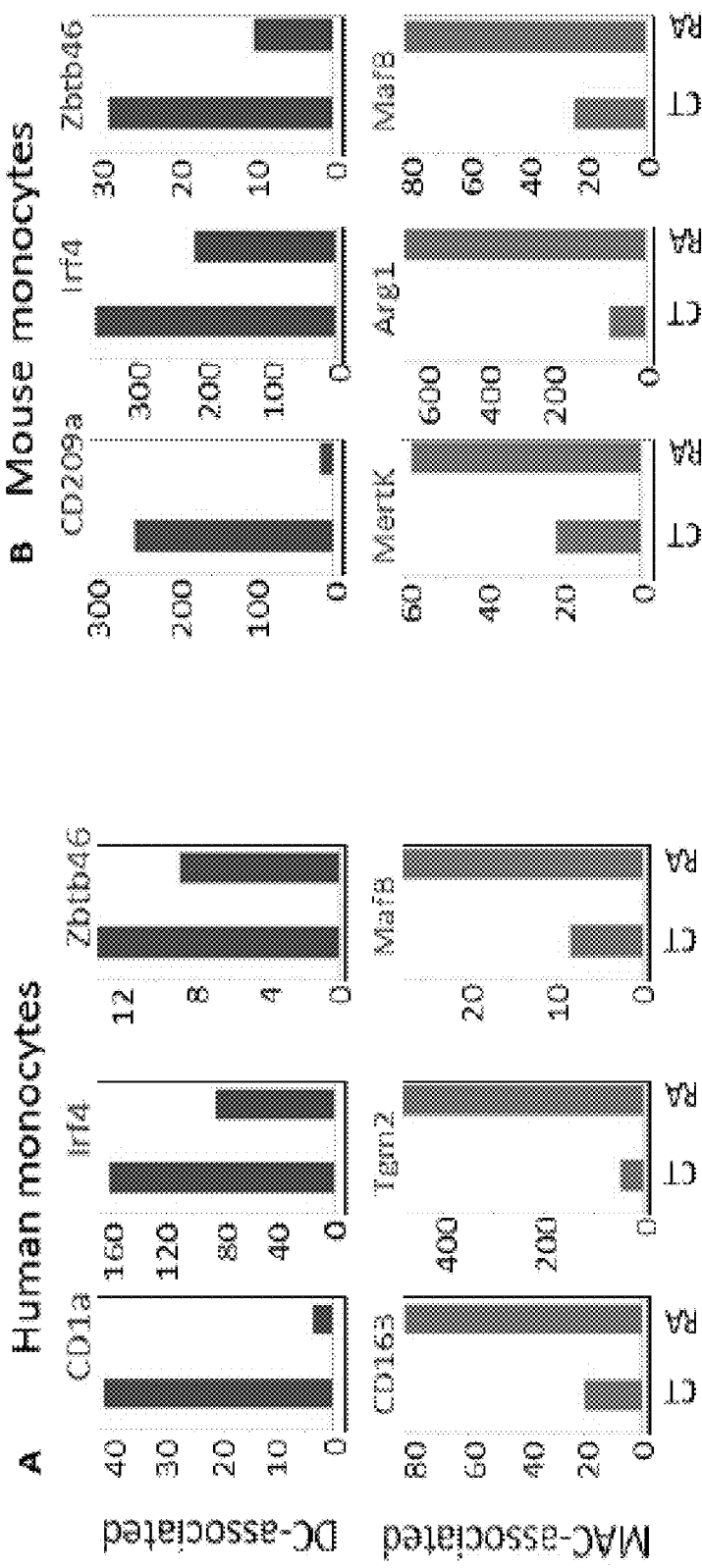
FIGS. 10A-10B illustrate that RA regulates DC- and macrophage-associated genes. Microarray (Affymetrix mouse gene 1.0ST, Y axis-expression value, linear scale×10, mean of 2 independent samples) based measurement of DC and macrophage-associated genes in human (FIG. 10A) and mouse (FIG. 10B) monocytes treated with RA and DMSO.
Figure 11:
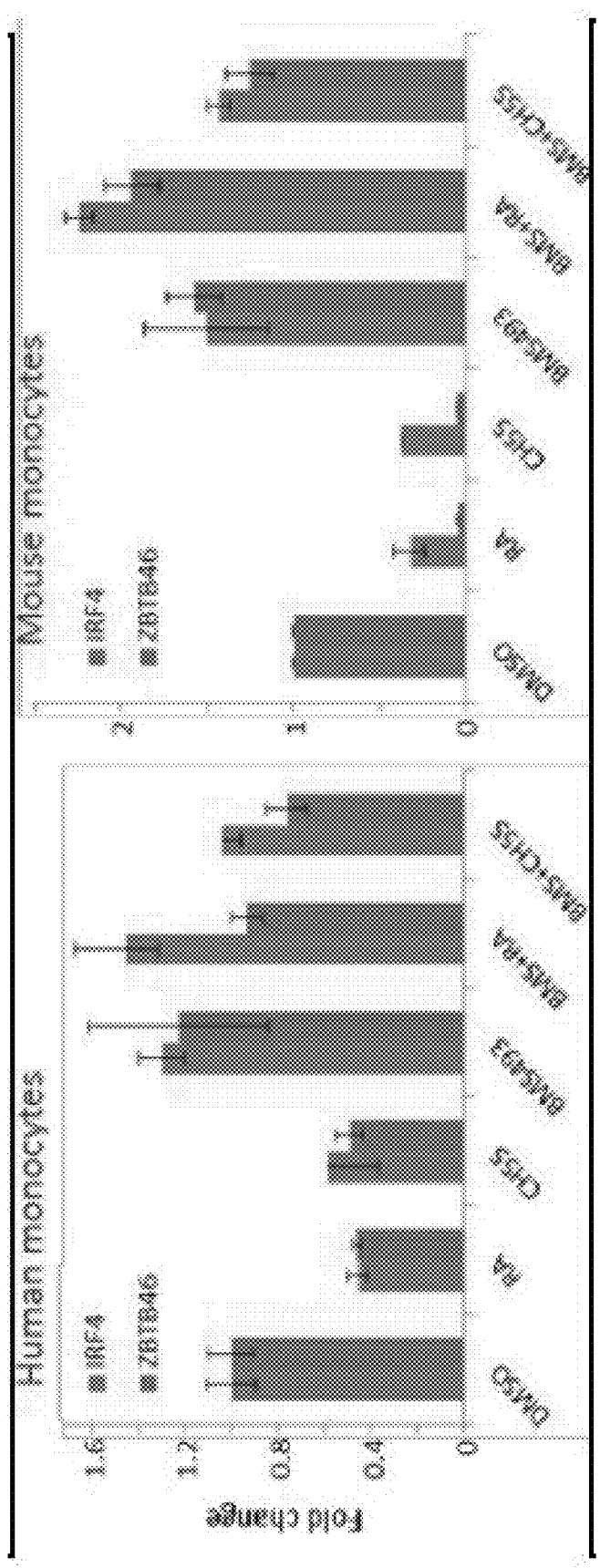
FIG. 11 illustrates that RA impacts monocyte differentiation. RT-QPCR for irf4 (promotes monocyte to DC differentiation) and Zbtb46 (expressed in all DCs irrespective of source) performed on human (left) and mouse (right) monocytes cultured under DC-promoting conditions (RPMI+10% FCS+GM-CSF+IL4) with RA, agonist of RA signaling (CH55), antagonist of RA signaling (BMS493) and DMSO (control). $P<0.05$ for agonist (RA and CH55) vs. DMSO. $P<0.05$ for agonist (RA and CH55) vs. agonist+antagonist (RA or CH55+BMS493). Data shown is representative of >4 independent experiments 3 replicates per condition in each experiment.
Figure 12:
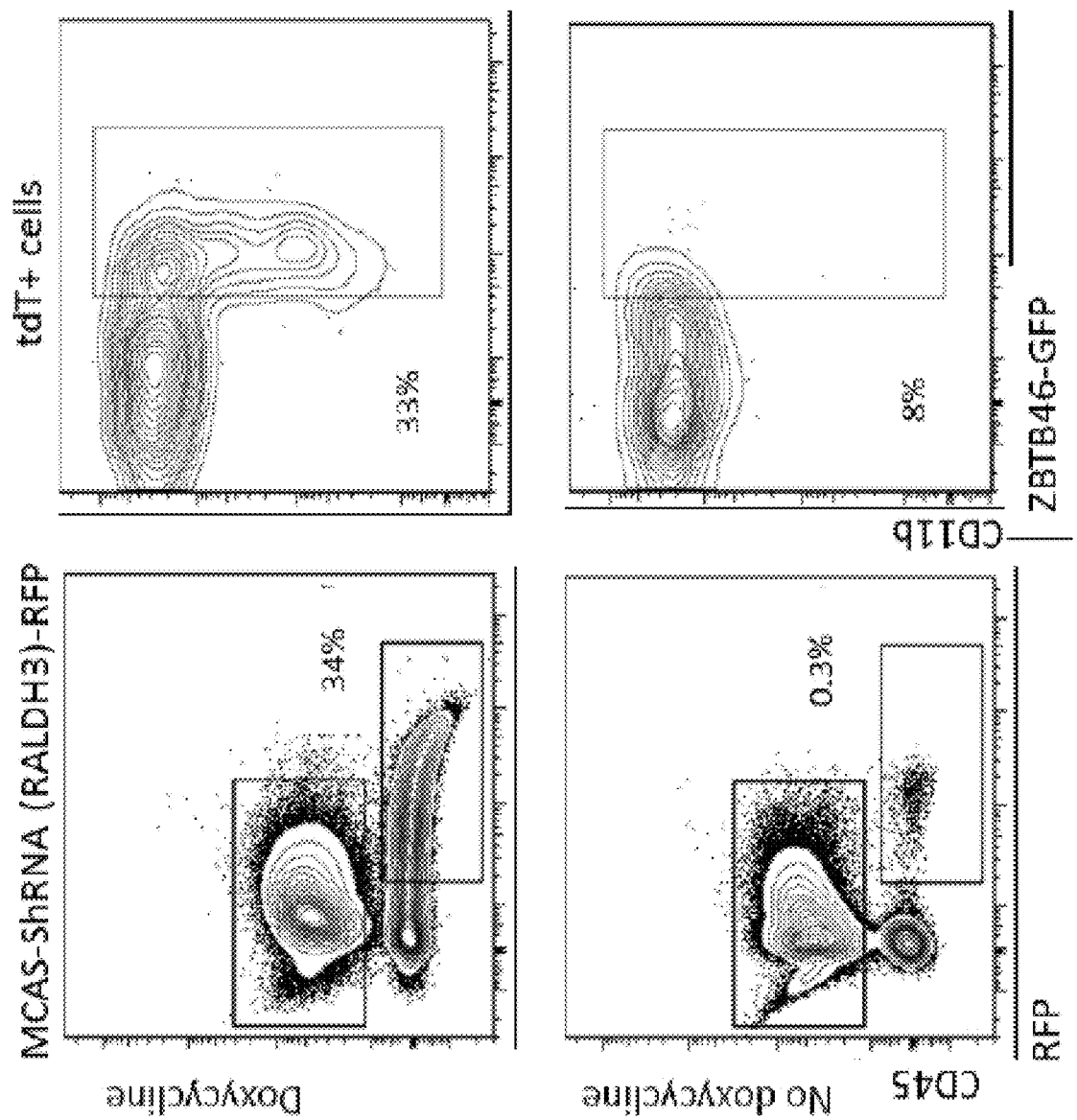
FIG. 12 illustrates that RA blocks monocyte to DC differentiation in tumors. MCAS-ShRNA(RALDH3)-RFP cells were transplanted into wild type (C57BL/6J) mice. Tumors were transplanted with monocytes from Lysm$^{Cre/+}$:Rosa$^{tdt/+}$:Zbtb46$^{gfp/+}$ mice. Mice were treated with doxycycline beginning the day of monocyte transplant and tumors analyzed after 6 days by FCM. RFP expression demonstrates induction of shRNA with doxycycline treatment. TDT expression distinguishes transplanted from host monocytes. Data is representative of 3 experiments.

Results described above suggested that monocytes preferentially generate TAMs but not DCs in sarcomas. Therefore, TME associated factors that may affect monocyte-differentiation were identified. Comparing gene expression profiles (microarray-based) of sarcoma-associated TAMs with tissue-resident macrophages revealed higher expression of cellular retinoic acid binding proteins (CRABP) in TAMS (FIGS. 8A-8B). Additionally, sarcomas expressed higher levels of RA-producing enzymes compared to surrounding tissue (FIG. 8C). Consistent with this, mass-spectrometry based measurements revealed significantly elevated RA in tumors (FIG. 8D). RA signaling has known roles in hematopoietic cell development. Therefore, the effects of RA were tested on the differentiation of human and mouse monocytes in vitro. Flow cytometry (FCM)-based analysis using established APC makers demonstrated that RA blocked DC but promoted macrophage differentiation (FIG. 9). Next, microarray-based gene expression analysis of monocyte-derived cells was performed in the aforementioned in vitro assay. This confirmed the FCM findings and revealed a significant reduction in the expression of DC associated genes in RA-treated cells (FIG. 10). In contrast, genes associated with macrophage differentiation were significantly upregulated by RA (FIG. 10). Of note, RA increased the expression of several genes associated with immunosuppressive and tumor promoting activities of TAM, such as Argl and TGM251 (FIG. 10). These effects of RA were blocked by RA antagonists and reproduced by RA-agonists (FIG. 11). Finally, the relevance of these findings was tested in vivo by generating MCAS cells with inducible (tetracycline-dependent) expression of RALDH3 (catalyzes RA production)-targeting short hairpin RNA (MCAS-shRNA(RALDH3)-RFP cell line). Reducing RA production in this setting led to enhanced generation of DCs from monocytes (FIG. 12). Therefore, high levels of RA in TME blocked monocyte differentiation into DCs.

Example 4—Tumor-Derived RA Blocks Anti-Tumor Immune Responses

Figure 4:
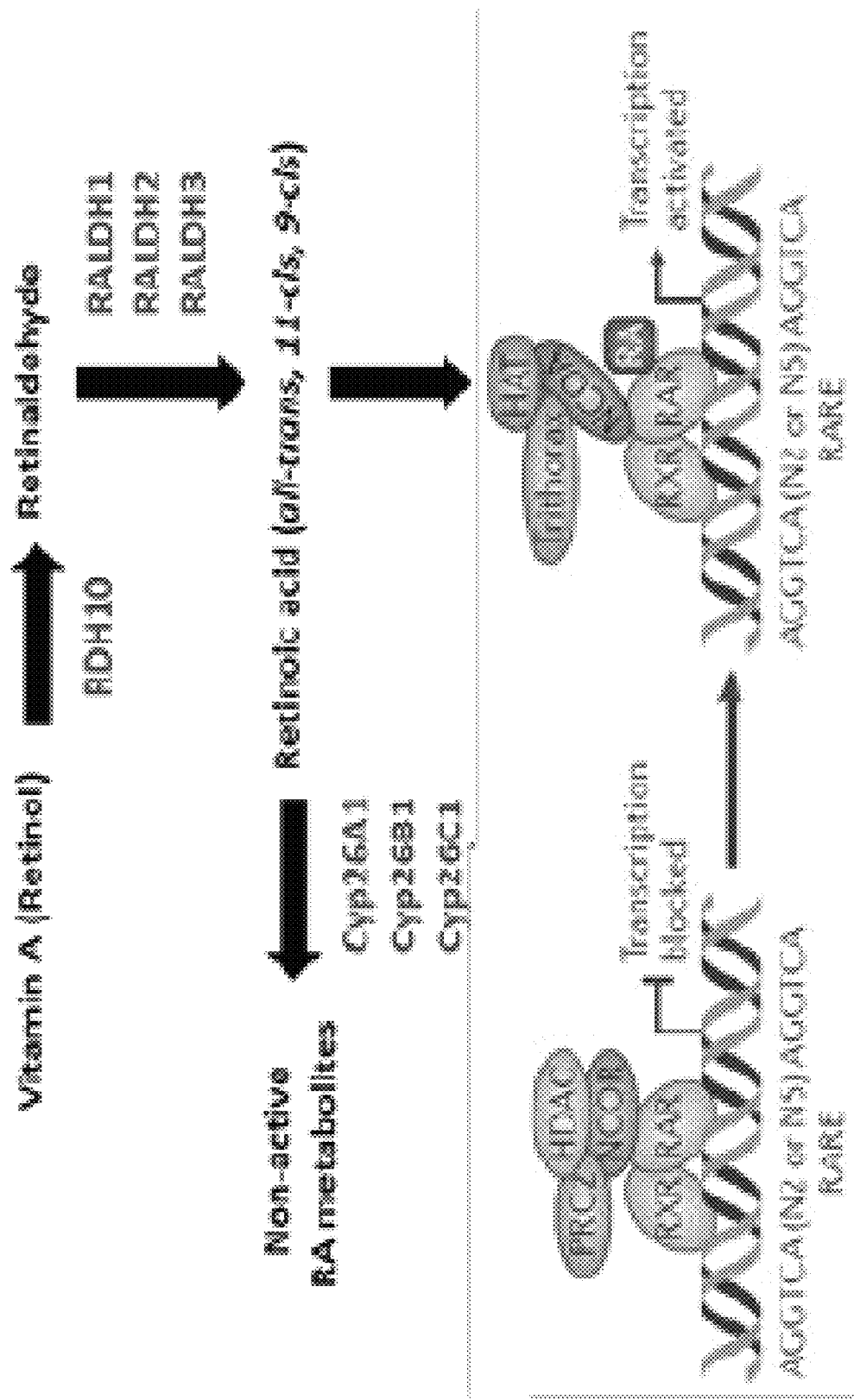
FIG. 4 is a schematic illustrating retinoic acid biosynthesis and activity. Major steps in the conversion of Vitamin A to bioactive retinoic acid and its subsequent metabolism to inert metabolites is shown. RDH: Retinol dehydrogenase; RALDH: Retinaldehyde dehydrogenase; Cyp26: Cytochrome P450, family 26. RARE: Retinoic acid response element.
Figure 5:
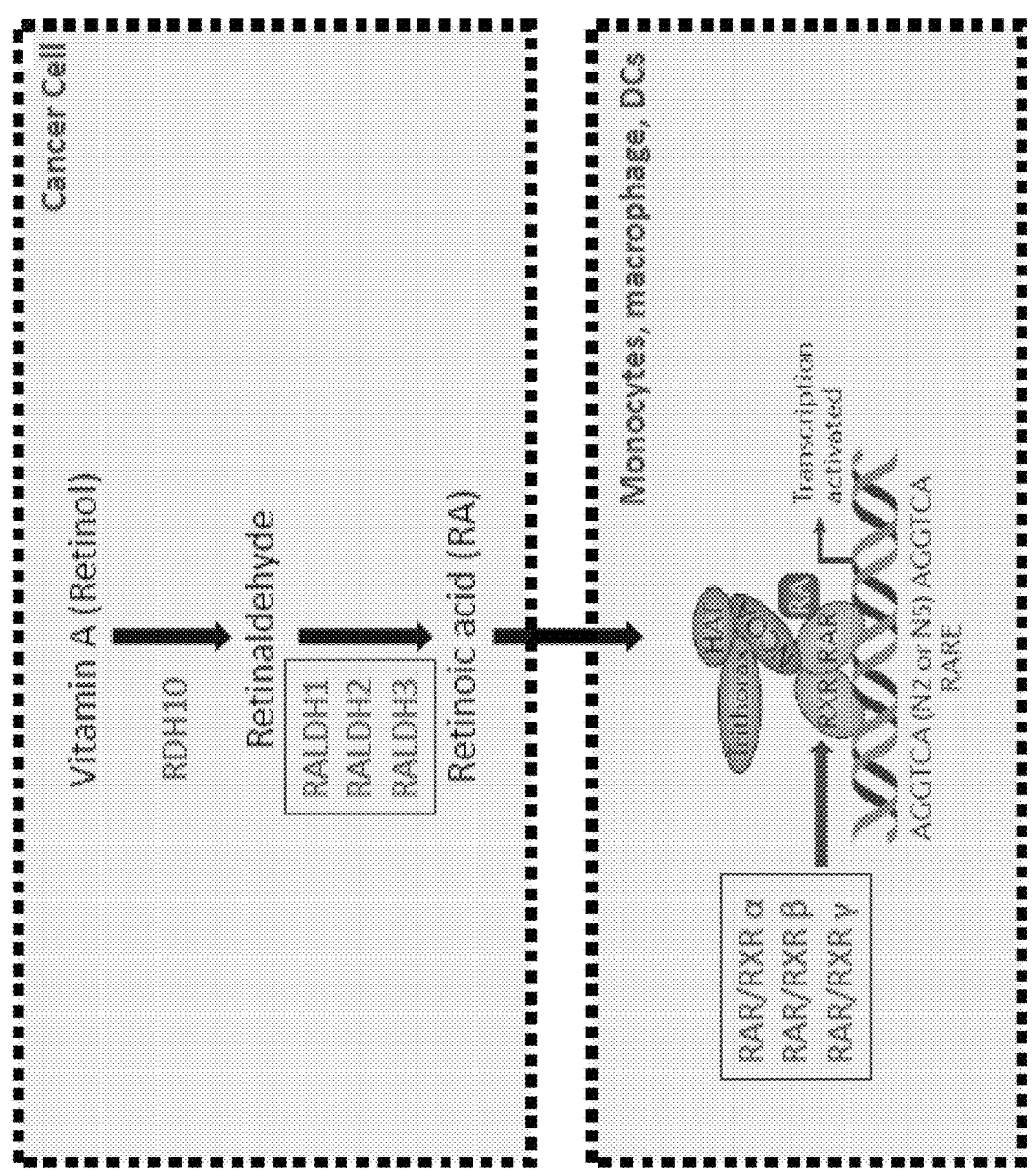
FIG. 5 is a schematic illustrating retinoic acid (RA) biosynthesis and its mode of action. RALDH are rate limiting enzymes for RA production. It was discovered by the present inventors that different tumors utilize different isoforms of RALDH. However, when one enzyme is knocked down, there is a compensatory increase in the other isoforms. There are non-specific inhibitors of RALDH, but not isoform-specific inhibitors. RA produced in one cell can be released into the microenvironment where it can act as a signaling molecule for neighboring cells. RA binds to cognate receptors that are transcription factors and are comprised of an RAR and RXR heterodimer. There are three RAR ($\alpha$, $\beta$, $\gamma$) and three RXR ($\alpha$, $\beta$, $\gamma$) isoforms, thereby generating diverse RAR-RXR heterodimer types. BMS493 is a pan-RAR inverse agonist, which blocks all RAR signaling.
Figure 13:
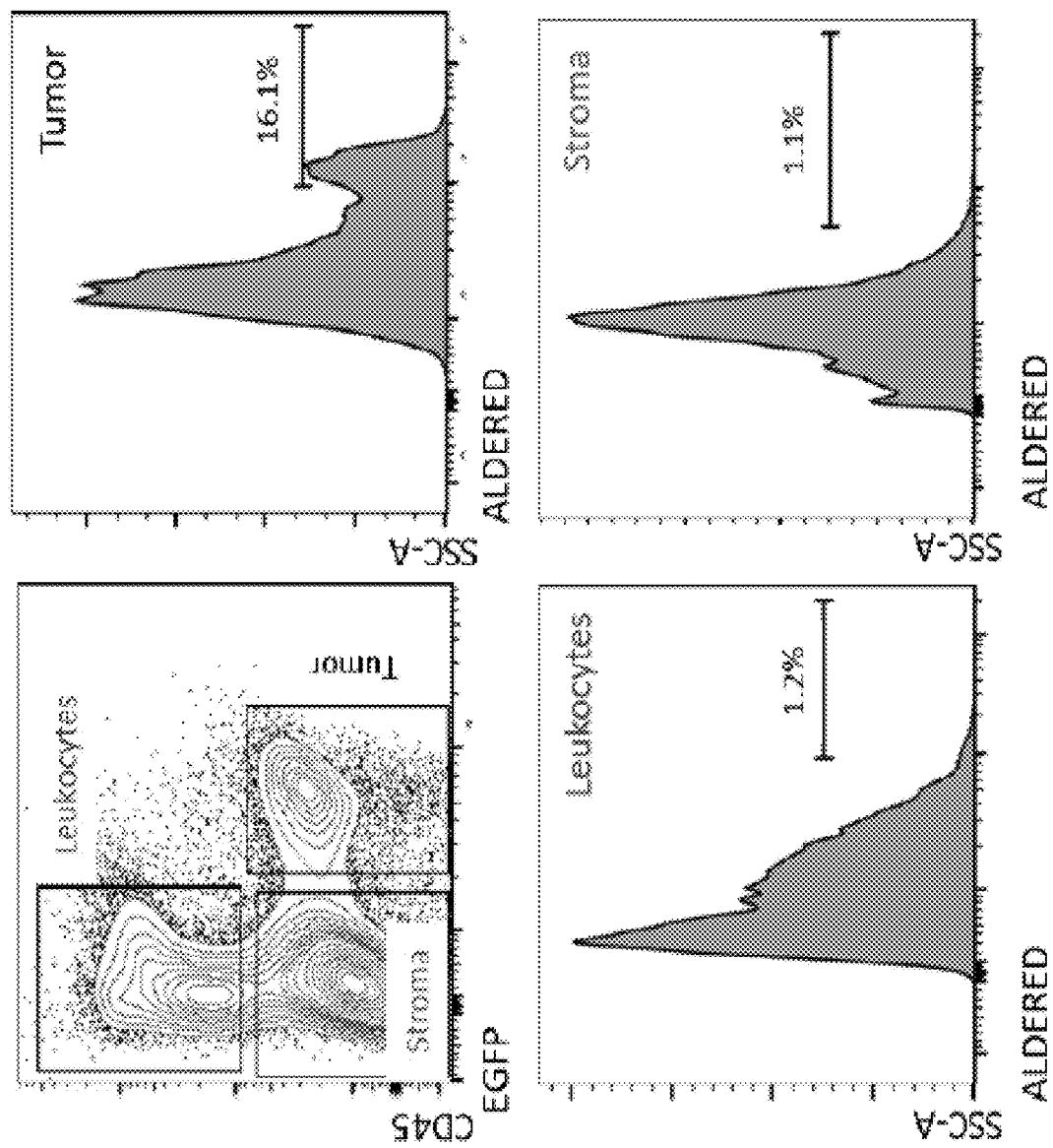
FIG. 13 illustrates RA production in TME. Single cell suspension from a murine synovial sarcoma were stained with indicated antibodies and subjected to aldered (Millipore) assay. Cells expressing RALDH enzymes become fluorescent (ALDERED+) in this assay. Tumor cells (EGFP) have significantly more ALDERED activity compared to leukocytes or other stromal cells. Similar results were obtained with other murine sarcomas. Data is representative of >10 experiments.
Figures 14A, 14B:
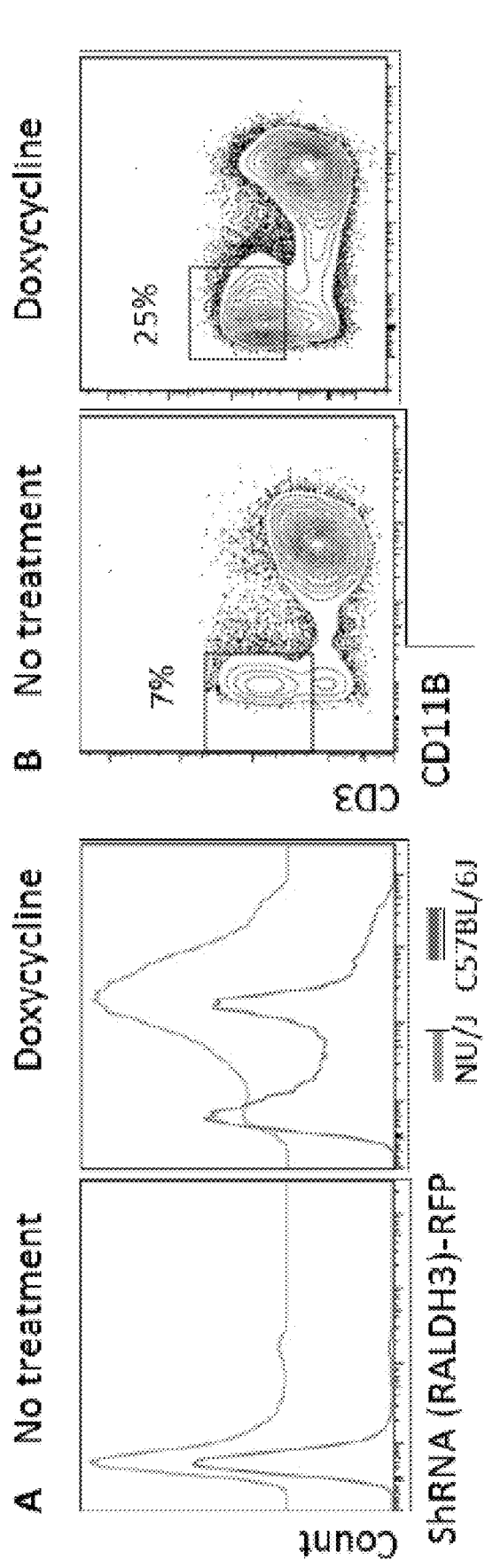
FIGS. 14A-14C illustrate that RA controls anti-tumor adaptive immune response.
Figure 14C:
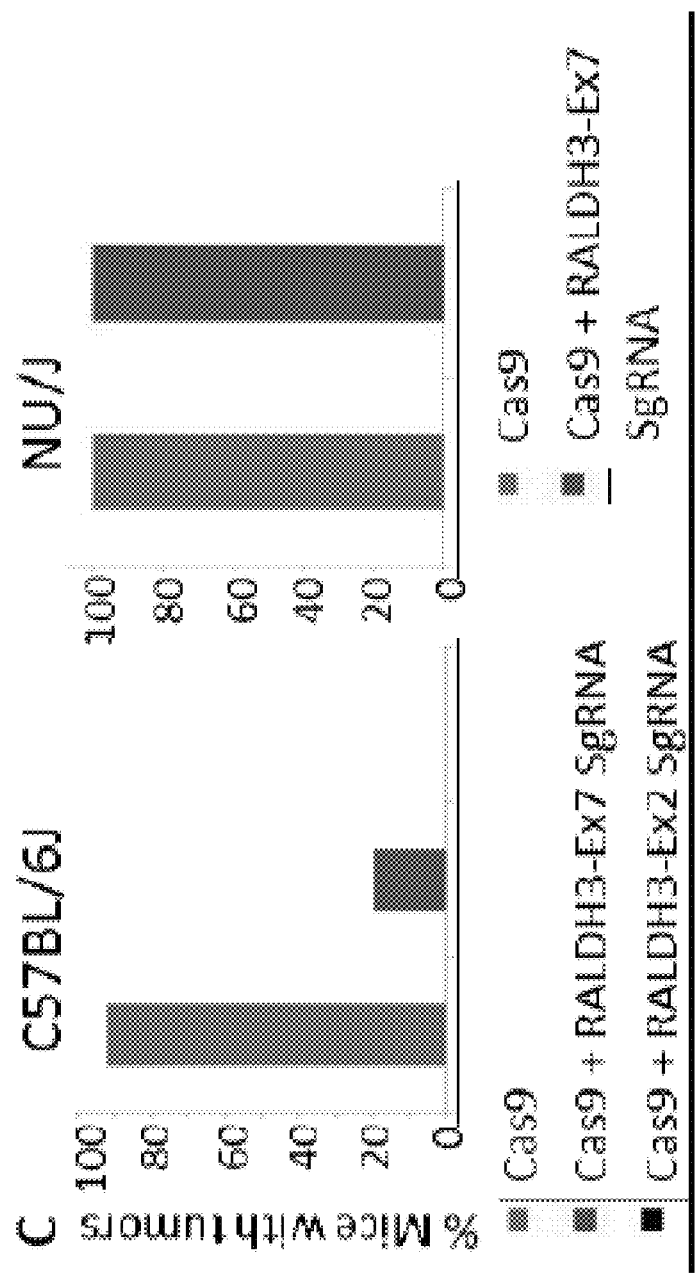
Figures 15A, 15B:
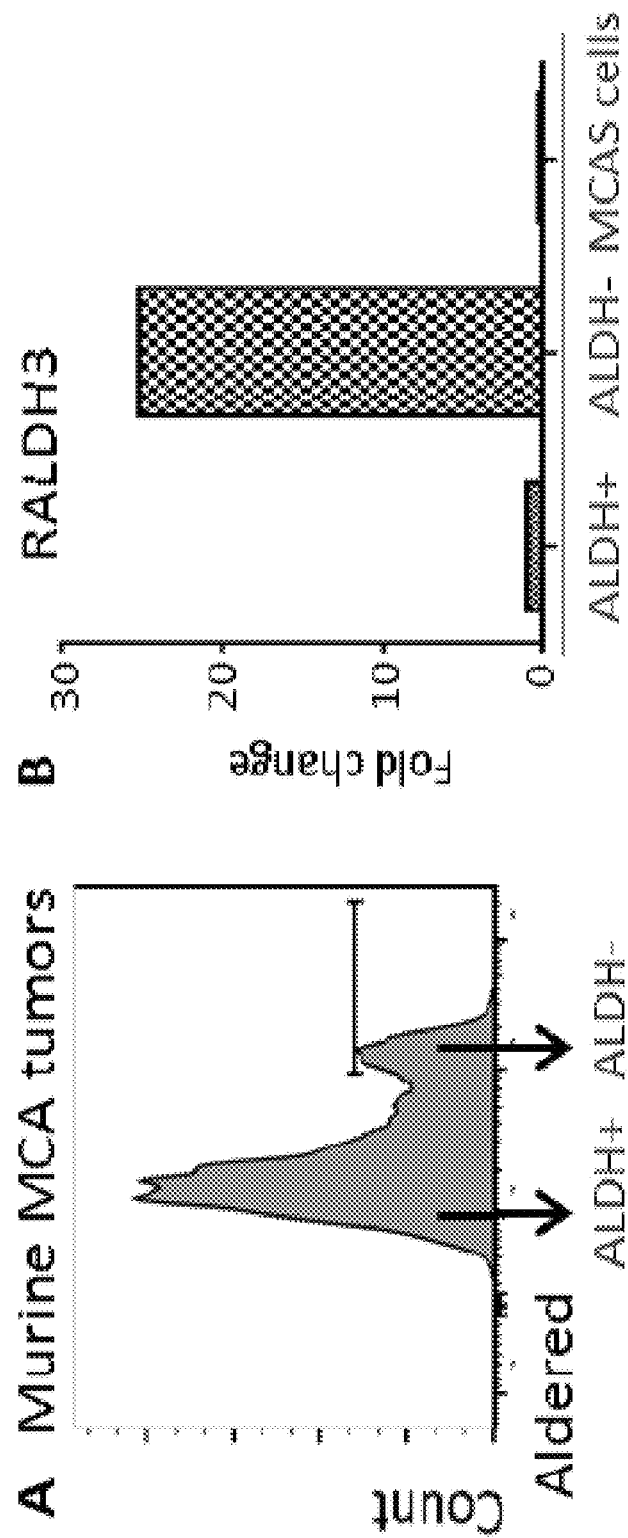
FIGS. 15A-15B illustrate that RA production is inducible in tumors.

To identify the source of RA in TME, the aldefluor assay (detects RA production in cells) was performed. In all three sarcoma models, tumor cells but not stromal cells produced the vast majority of RA (FIG. 13). The conversion of retinaldehyde to RA is the rate limiting step in RA biogenesis that is catalyzed by one of three functionally redundant enzymes; RALDH1, RALDH2, and RALDH3 (FIG. 4). RA producing cells in MCAS-fibrosarcomas expressed high levels of RALDH3 (FIGS. 15A-15B). Reducing RALDH3 levels in MCAS-shRNA-RALDH3 tumors led to robust T cell infiltration and a selective reduction of shRNA expressing (RFP+) tumor cells in immunocompetent B6 but not immunodeficient NU/J mice (FIGS. 14A-14B). To attain a more complete loss of function, the RALDH3 gene was inactivated in MCAS cells by CRISPR/CAS9. RALDH3 knockout cells failed to grow in immunocompetent, but not immunodeficient mice (FIG. 14C). Mice that rejected RALDH3 deficient cells became immune to subsequent challenge by parental MCAS cell lines.

Example 5-IL13 Induces RA Production in Tumor Cells

Figures 16A, 16B:
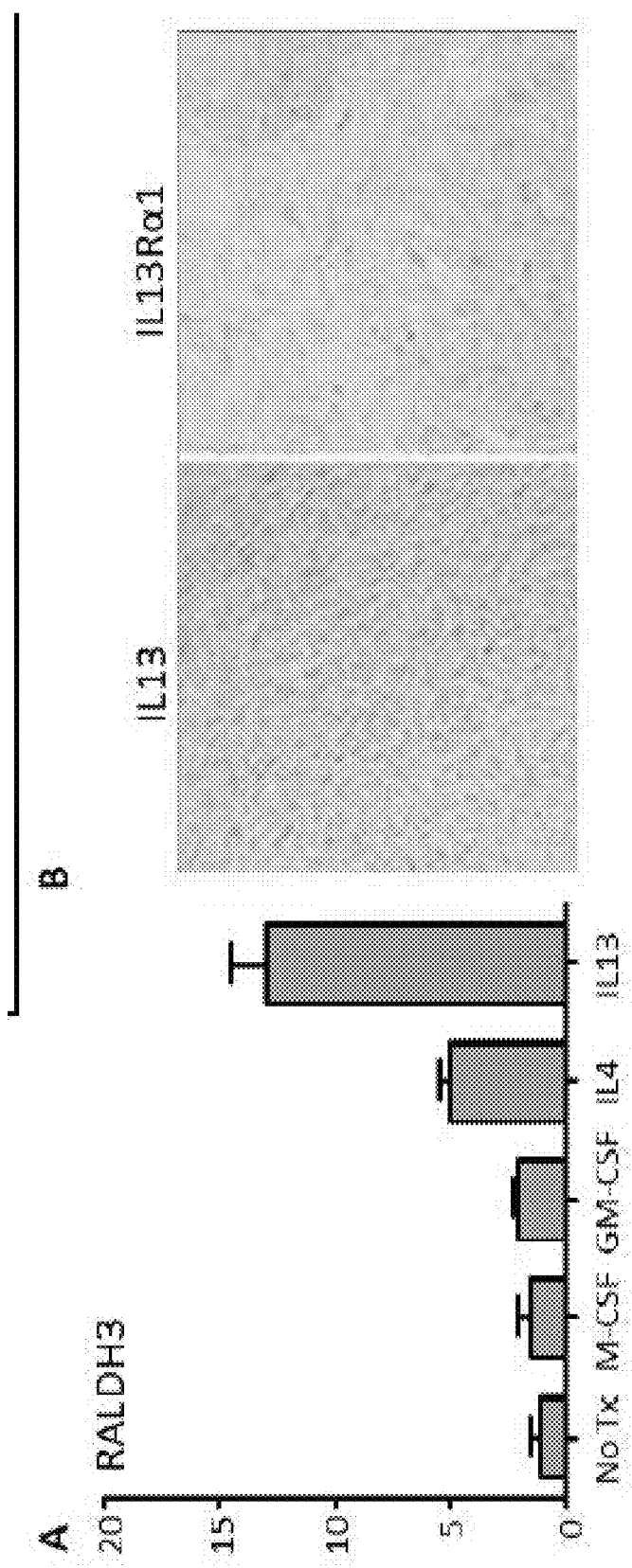
FIGS. 16A-16C show 1L13 and RALDH expression.
Figure 16C:
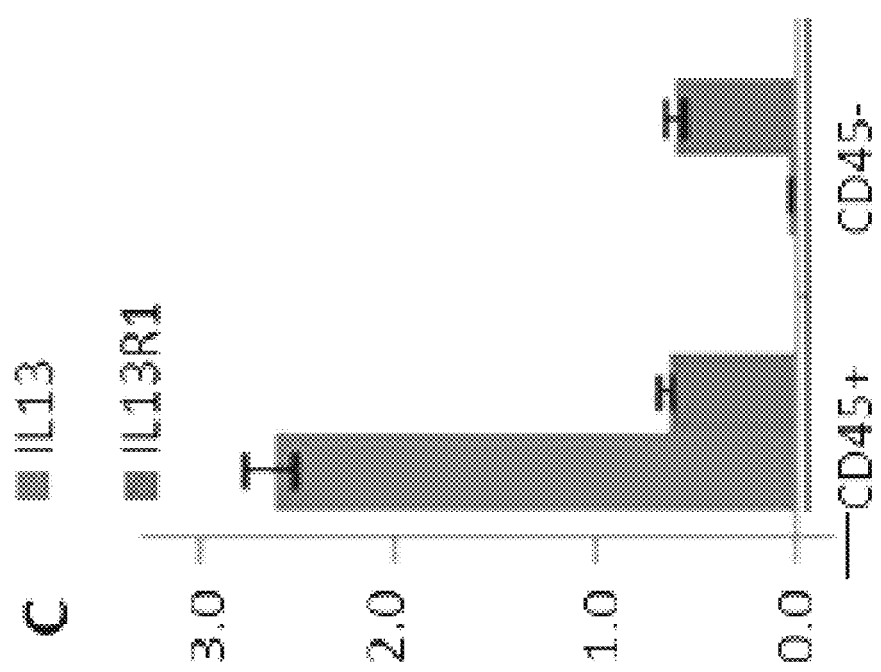
Figure 17:
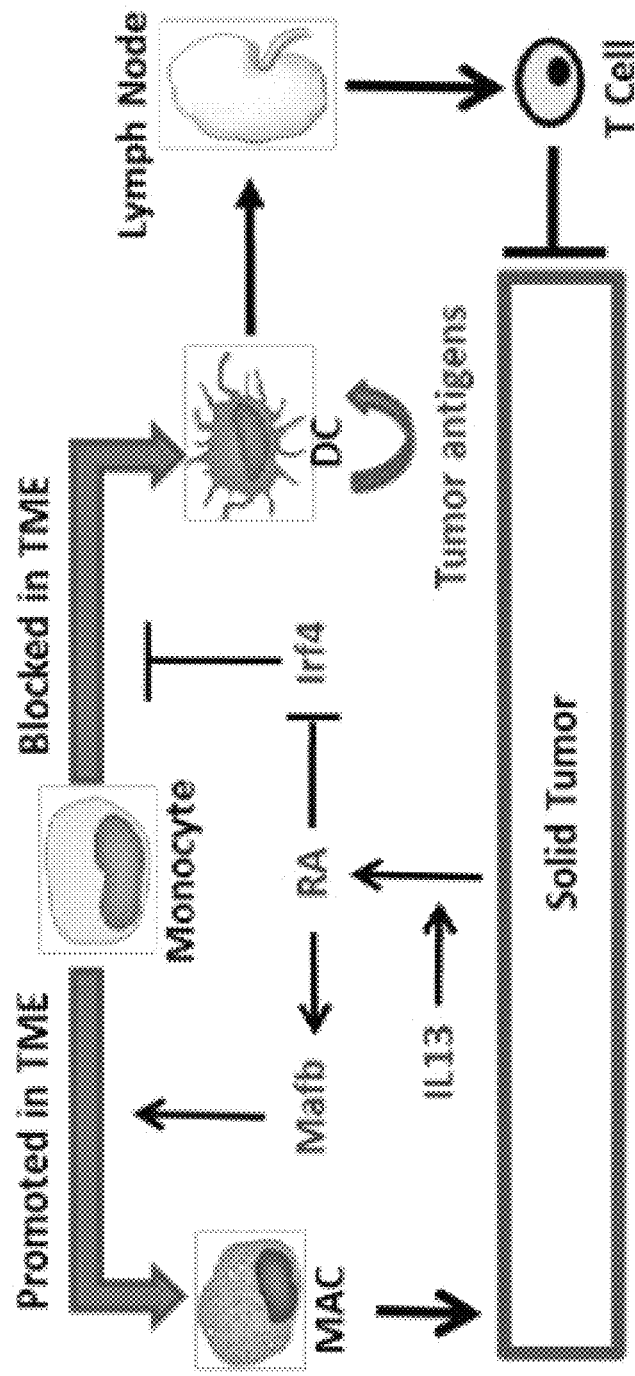
FIG. 17 is a schematic illustrating that 1L13 induces RA production by tumor cells, which blocks DC and promotes TAM differentiation from TME monocytes.
Figure 18:
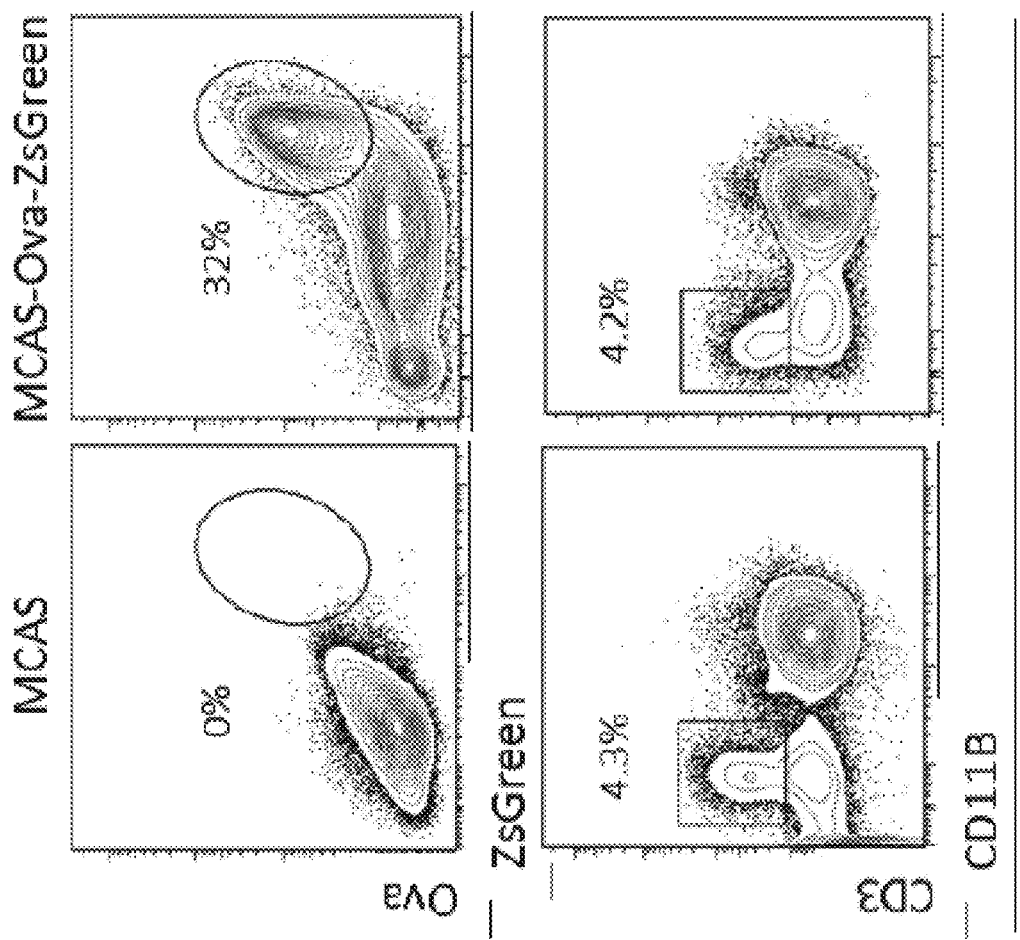
FIG. 18 illustrates expression of a model antigen in the tumor. OVA-associated SIINFEKL peptide and ZsGreen reporter were expressed in MCAS cell lines. The resulting MCAS-Ova-ZsGreen cells were transplanted into B6 mice and tumors analyzed after 7 days. SIINFEKL peptide bound to MHC-I molecule was detected by fluorescent antibody (top). Data is representative of 3 experiments.
Figure 19:
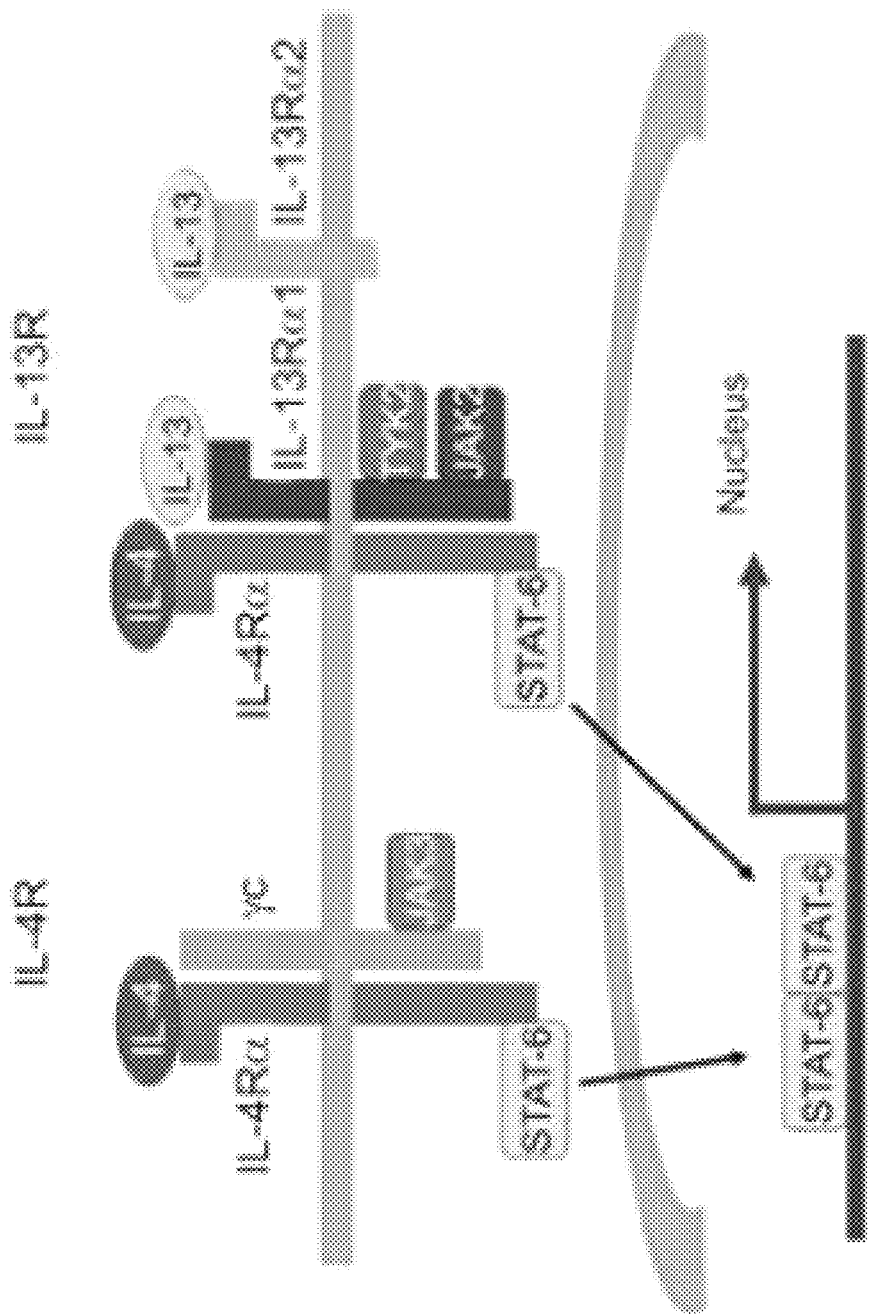
FIG. 19 illustrates IL13 signaling (from Oh et al. *Eur. Respir. Rev. Off J. Eur. Respir. Soc.* 19, 46-54 (2010)). IL4 and IL13 share receptor subunits and control downstream gene expression via STAT transcription factors.

The aldefluor assay demonstrated fibrosarcomas to be heterogeneous for RA production (FIGS. 13 and 15). Furthermore, MCAS cell lines expressed very low levels of RALDH3, which was dramatically upregulated upon transplantation (FIG. 15). Aldefluor positive and negative cells were purified from murine fibrosarcomas and were transplanted into syngeneic B6 mice. Tumors derived from both types of cells generated both aldefluor positive and negative cells. This indicated the existence of an environmental signal in the TME that induces RA production in tumor cells. Th2 cytokines such as IL4 and IL13 can promote the differentiation of monocytes into either immunostimulatory DCs or immunosuppressive TAMS. Therefore, it was reasoned that tumors might induce RA production in the presence of IL4 or IL13 to block DC and promote TAM differentiation. To test this, MCAS cell lines were treated with cytokines promoting macrophage and DC differentiation and measured the expression of RALDH enzymes. While IL4 and IL13 both induced the expression of RALDH3, IL13 was more potent in this regard (FIG. 16A). IL13 and its receptor IL13Rα1 were also detected in murine sarcomas by IHC (FIG. 16B). Notably, while the IL13 receptor expression was similar in tumor cells and infiltrating leukocytes, IL13 cytokine was predominantly produced by leukocytes (FIG. 16C).

Example 6-Targeting IL13 for Signaling for Tumor Immunotherapy

Figures 20A, 20B:
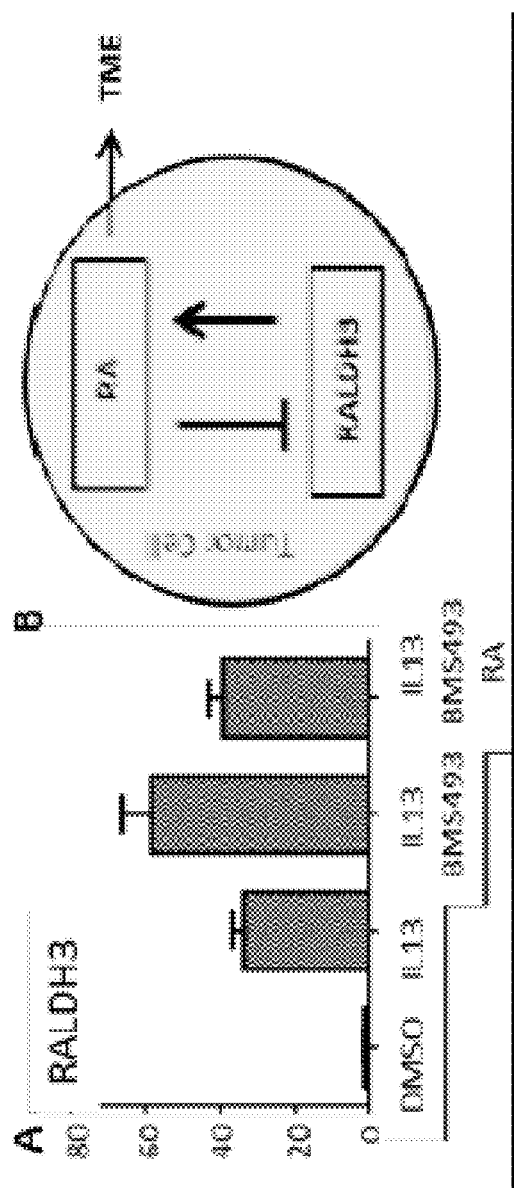
FIGS. 20A-20B illustrate negative regulation of RALDH3 by RA.
Figure 21:
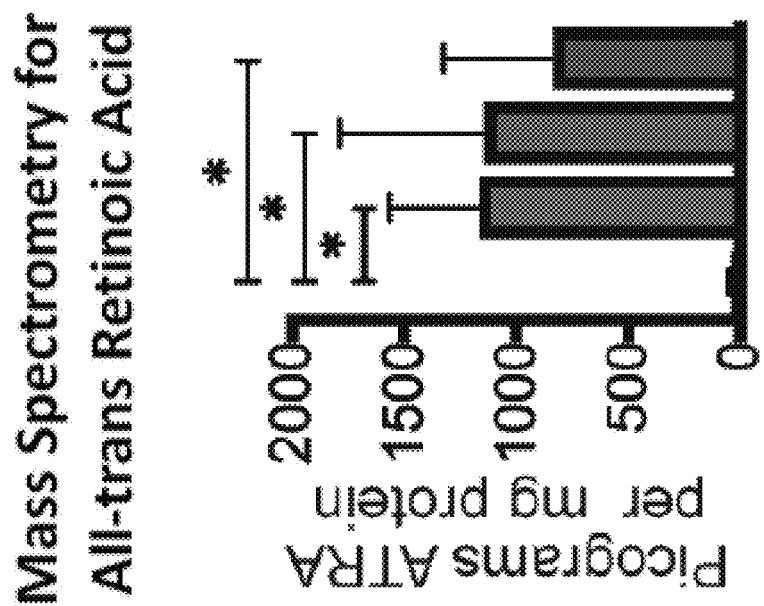
FIG. 21 illustrates that ATRA levels are significantly higher in sarcomas compared to surrounding tissue. Tumor or normal skeletal muscle tissue was dissected out from euthanized mice. The tissues were stored in a −80 degree Celsius freezer. All trans retinoic acid (ATRA) levels were measured by liquid chromatography/mass spectrometry.
Figure 22:
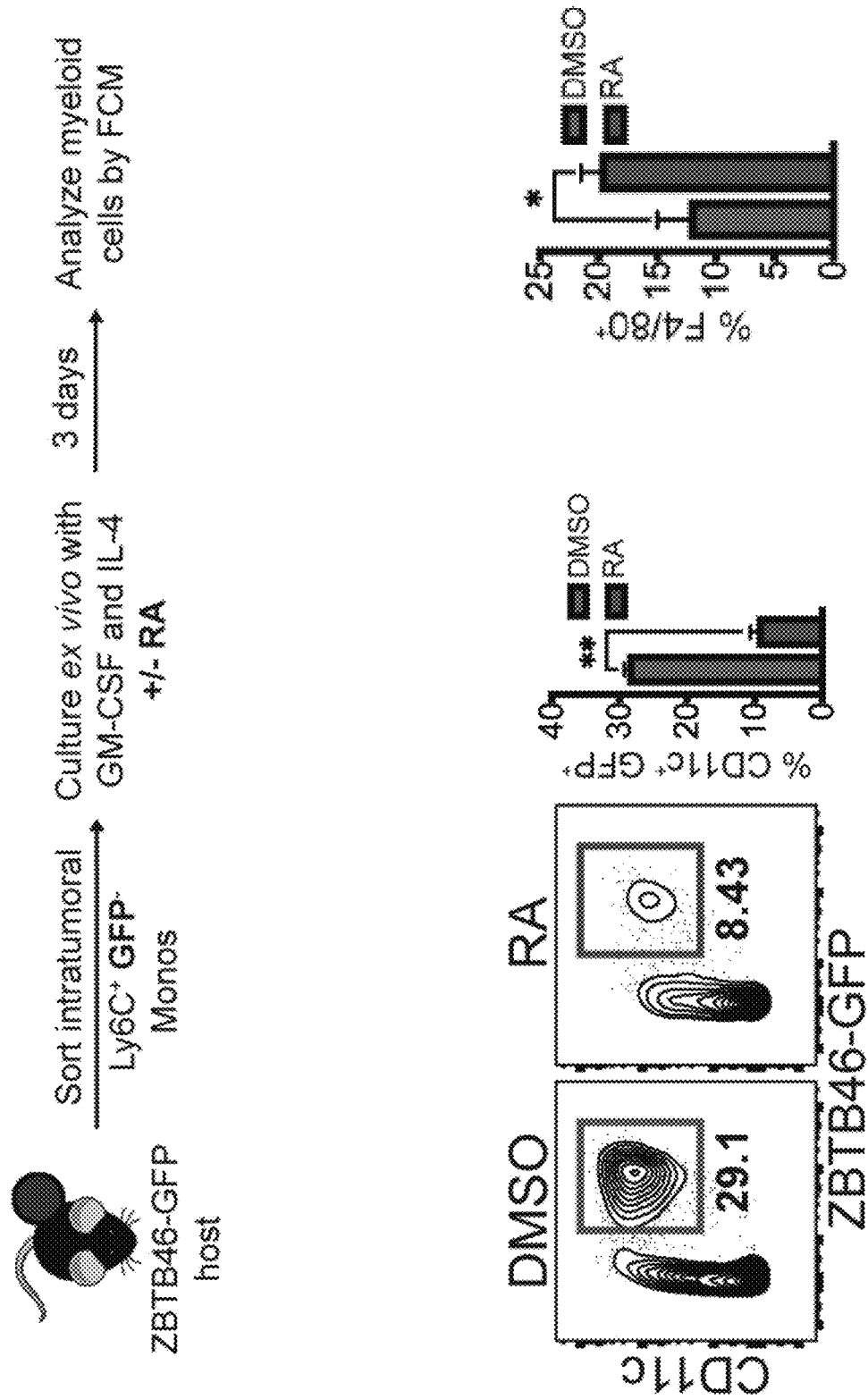
FIG. 22 illustrates that RA inhibits DC and promotes macrophage differentiation in sorted tumor monocytes. Ly6C+ZBTB46-GFP-monocytes were purified (by cell sorting) from fibrosarcoma (FS) tumors generated by syngeneic transplant of FS cells into ZBTB46-GFP mice. The purified monocytes were cultured for 3d with GM-CSF (20 ng/mL) and IL-4 (20 ng/mL). DMSO or RA (100 nM) was added at the onset of culture. Contour plots and frequencies are shown from monocytes sorted from n=3 FS tumors harvested 14d post-transplant. Data are representative of three independent experiments.
Figure 23:
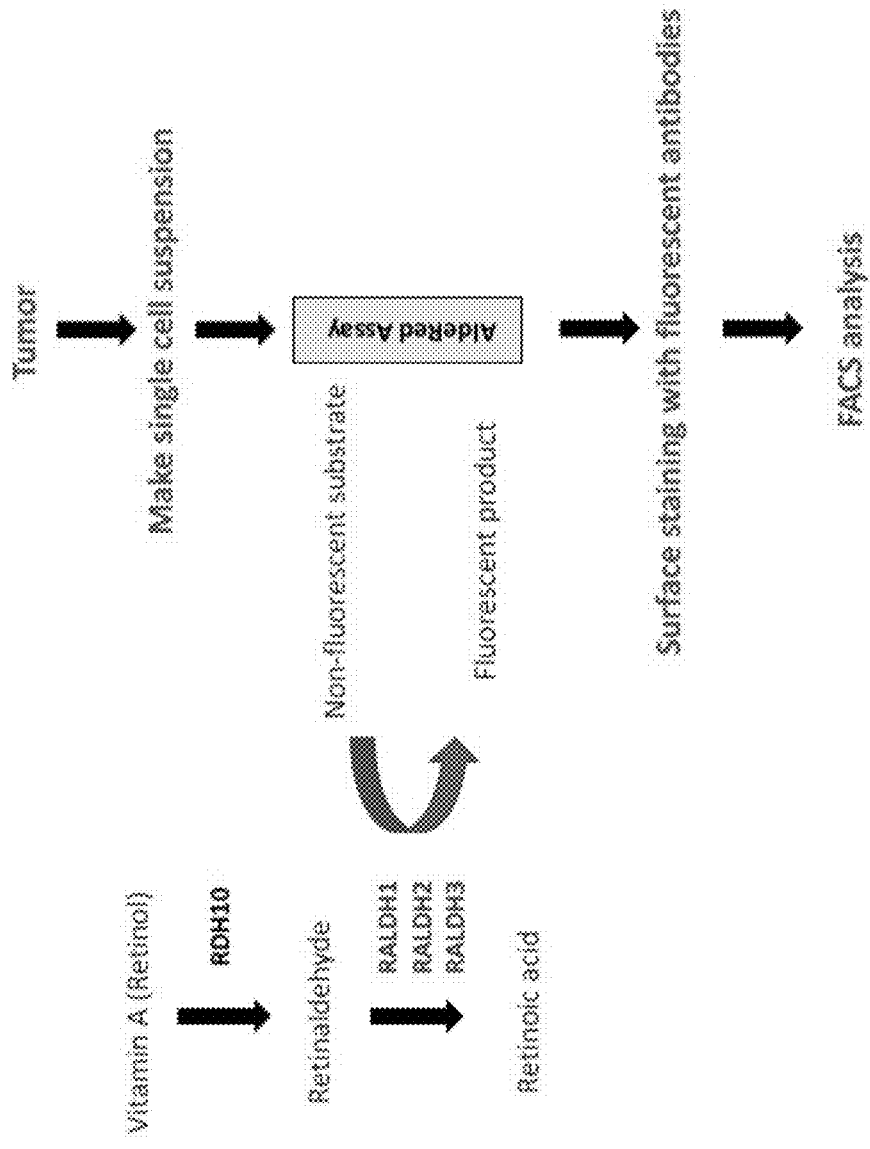
FIG. 23 illustrates an assay to identify RA producing cells in sarcomas.
Figures 25A, 25B:
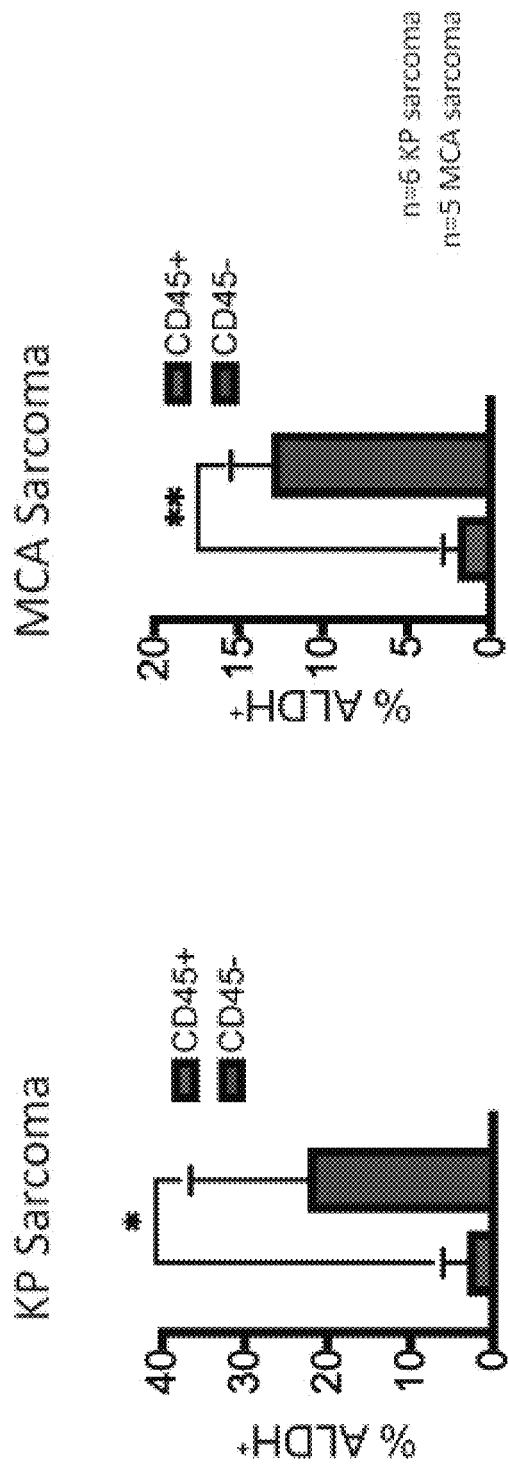
FIGS. 25A-25C illustrate that the majority of RA is produced by tumor cells. ALDEFLUOR assay (similar to ALDERED described above with a different fluorophore) was performed on mouse undifferentiated pleomorphic sarcoma (UPS, FIG. 25A), mouse FS (FIG. 25B), and human UPS (FIG. 25C).
Figure 25C:
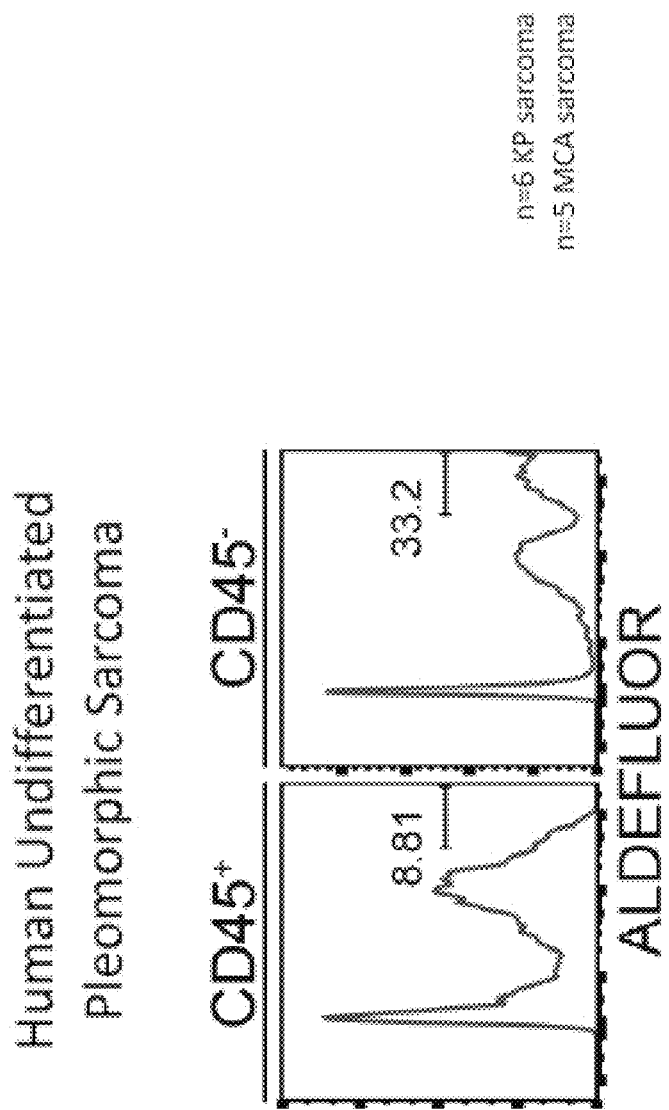

IL13 signaling promotes RA production in sarcoma cells. In addition to inducing RALDH3, IL13 treatment of sarcoma cells induces several genes with known roles in tumor progression. Therefore, blocking IL13 signaling may have additional anti-tumor effects beyond its impact on RA. Additionally, blocking RA signaling in tumor cells was found to lead to compensatory increases in RALDH3 expression (FIG. 20). This type of feedback loops are common in metabolic enzymes. Without wishing to be bound by theory, this feedback loop suggests that RA production is important for the tumor.

Example 7-CRISPR-Cas9 Deletion of RA Producing Enzymes

Figure 26:
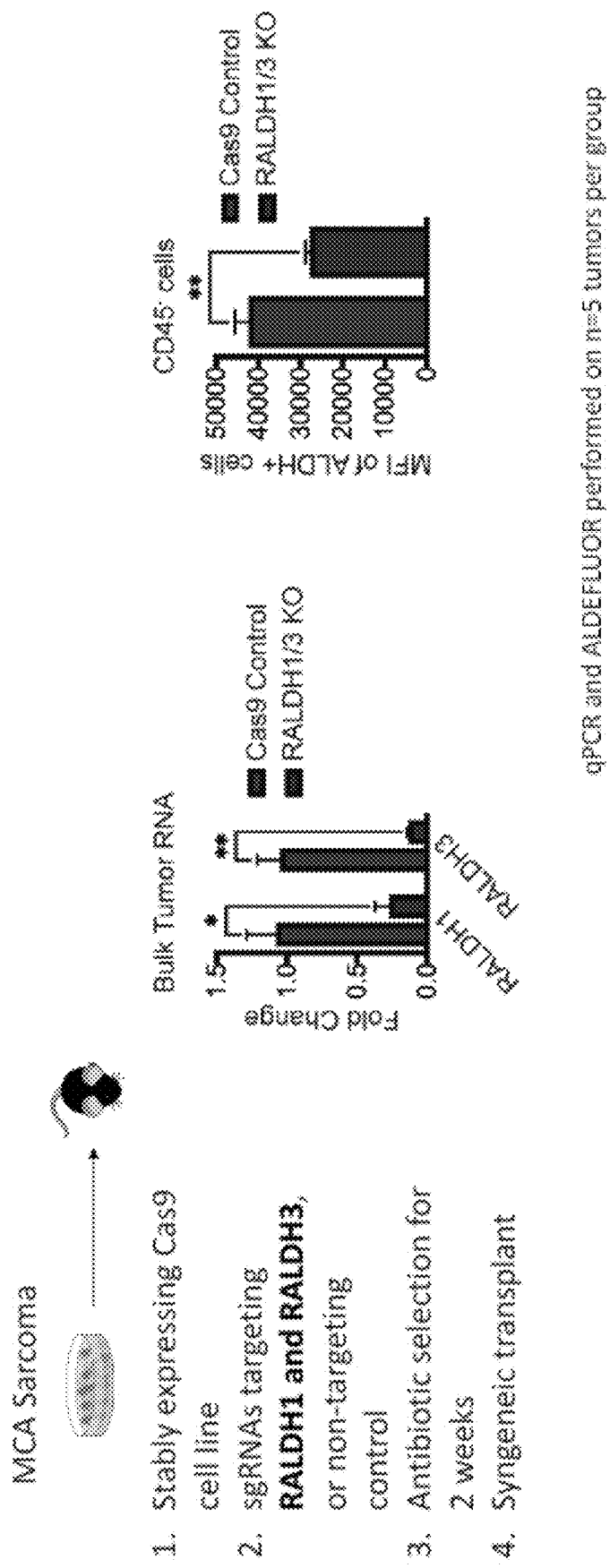
FIG. 26 illustrates CRISPR-Cas9 deletion of RA producing enzymes. CRISPR-Cas9 system was used to delete both Raldh1 and Raldh3 genes to reduce RA production in murine FS cells (also denoted as 'MCA' sarcoma as these FS tumor cells are derived from murine sarcomas generated by exposure to methylcholanthrene, or MCA, many years ago and carried forward as a cell line). The bar graph on the left shows expression of Raldh1 and Raldh3 by qPCR in RALDH1/3 double knockout (DKO) vs. Cas9 control tumors are shown (n=5 tumors per group). Expression is normalized to Hprt. Data representative of two independent experiments. The bar graph on the right shows median fluorescence intensity of RALDH activity in CD45-ALDH+ cells assessed by ALDEFLUOR assay in RALDH1/3 DKO vs. Cas9 Control FS tumors.

The CRISPR-Cas9 deletion of RA producing enzymes is illustrated in FIG. 26. A CRISPR-Cas9 system was used to delete both Raldh1 and Raldh3 genes to reduce RA production in murine FS cells (also denoted as 'MCA' sarcoma as these FS tumor cells are derived from murine sarcomas generated by exposure to methylcholanthrene, or MCA, many years ago and carried forward as a cell line). The bar graph on the left of FIG. 26 shows expression of Raldh1 and Raldh3 by qPCR in RALDH1/3 double knockout (DKO) vs. Cas9 control tumors are shown (n=5 tumors per group). Expression is normalized to Hprt. Data representative of two independent experiments. The bar graph on the right shows median fluorescence intensity of RALDH activity in CD45-ALDH+cells assessed by ALDEFLUOR assay in RALDH1/3 DKO vs. Cas9 Control FS tumors.

Figure 27:
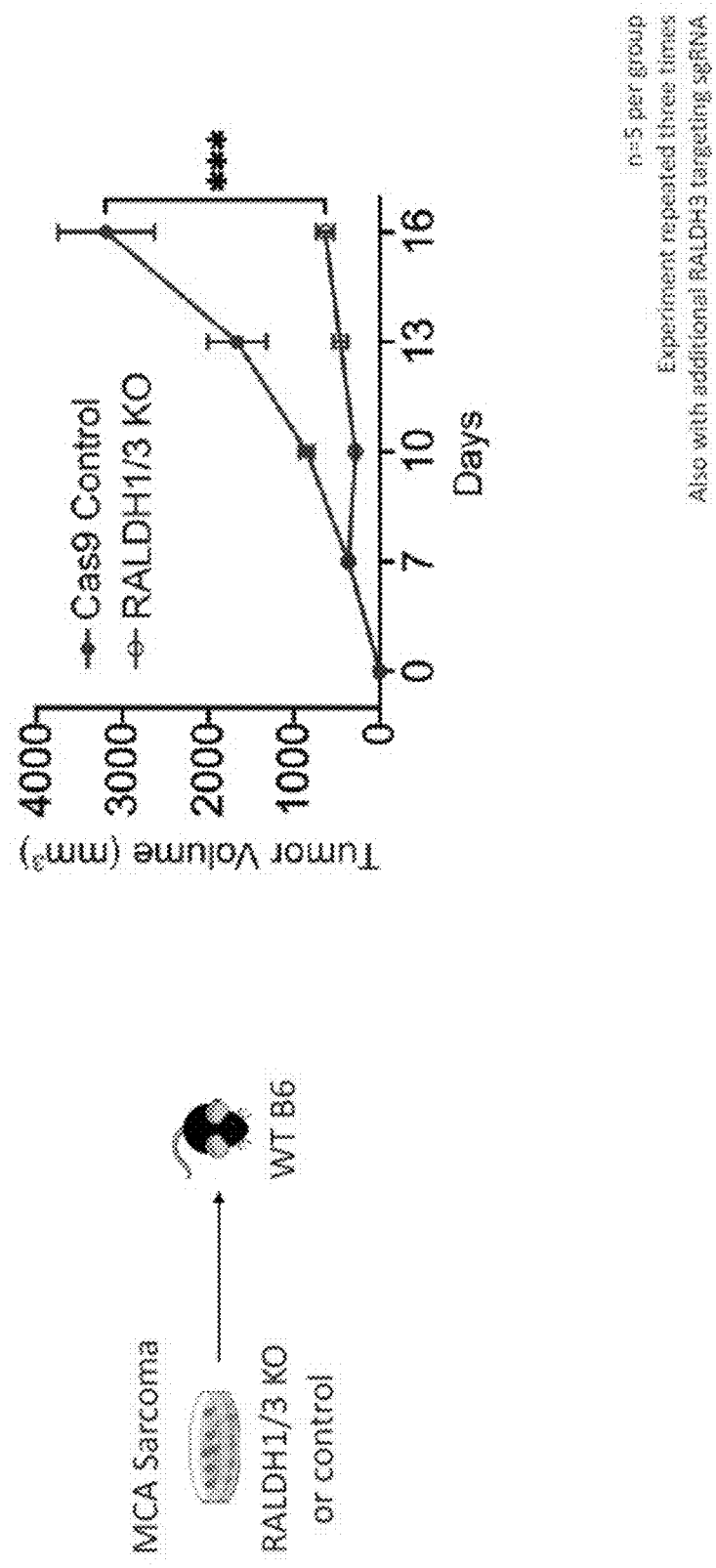
FIG. 27 illustrates RALDH1/3 KO sarcomas demonstrate inhibited growth in immunocompetent mice. A tumor growth curve of RALDH1/3 DKO or Cas9 Control FS tumors implanted subcutaneously into syngeneic C57BL/6 mice is shown. Tumor volume was measured every three days starting at 7d post-implantation. n=8 tumors per group; data are representative of three independent experiments.

Example 8-RALDH1/3 KO Sarcomas Demonstrate Inhibited Growth in Immunocompetent Mice A tumor growth curve of RALDH1/3 DKO or Cas9 Control FS tumors implanted subcutaneously into syngeneic C57BL/6 mice is shown in FIG. 27. Tumor volume was measured every three days starting at 7d post-implantation. n=8 tumors per group; data are representative of three independent experiments.

Figure 28:
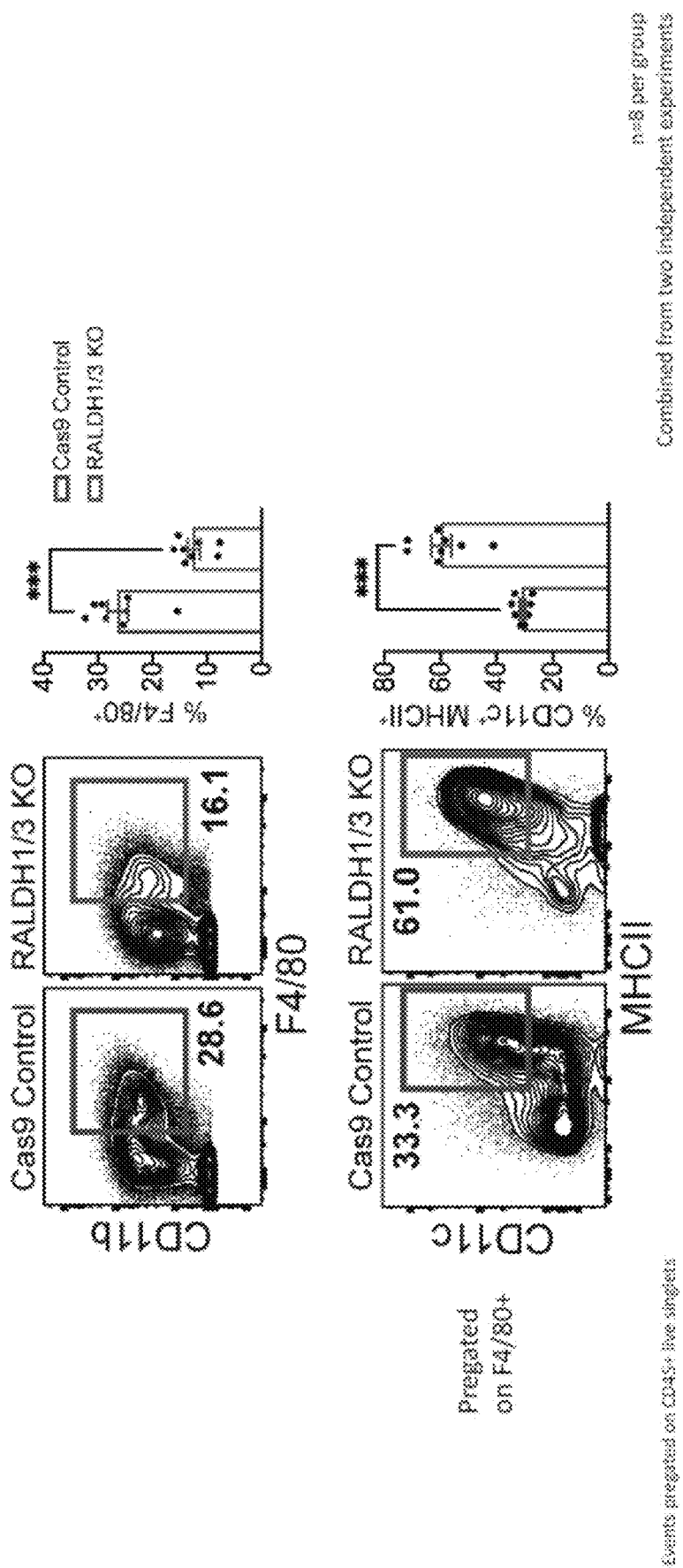
FIG. 28 illustrates that inhibiting tumor-derived RA decreases suppressive macrophage generation in vivo. Top left panel shows the frequency of CD11b+F4/80+tumor-associated macrophages (TAMs) in RALDH/3 DKO or Cas9 Control FS tumors. Top right bar graph shows the frequency of TAMs (n=8 tumors per group). Data representative of three independent experiments. Bottom left panel shows the frequency of TAMs expressing both CD11c and MHCII (pregated on CD11b+F4/80+) in RALDH1/3 DKO or Cas9 Control FS tumors. Bottom right panel shows the frequency of these cells (n=8 tumors per group). Data are representative of three independent experiments.
Figure 29:
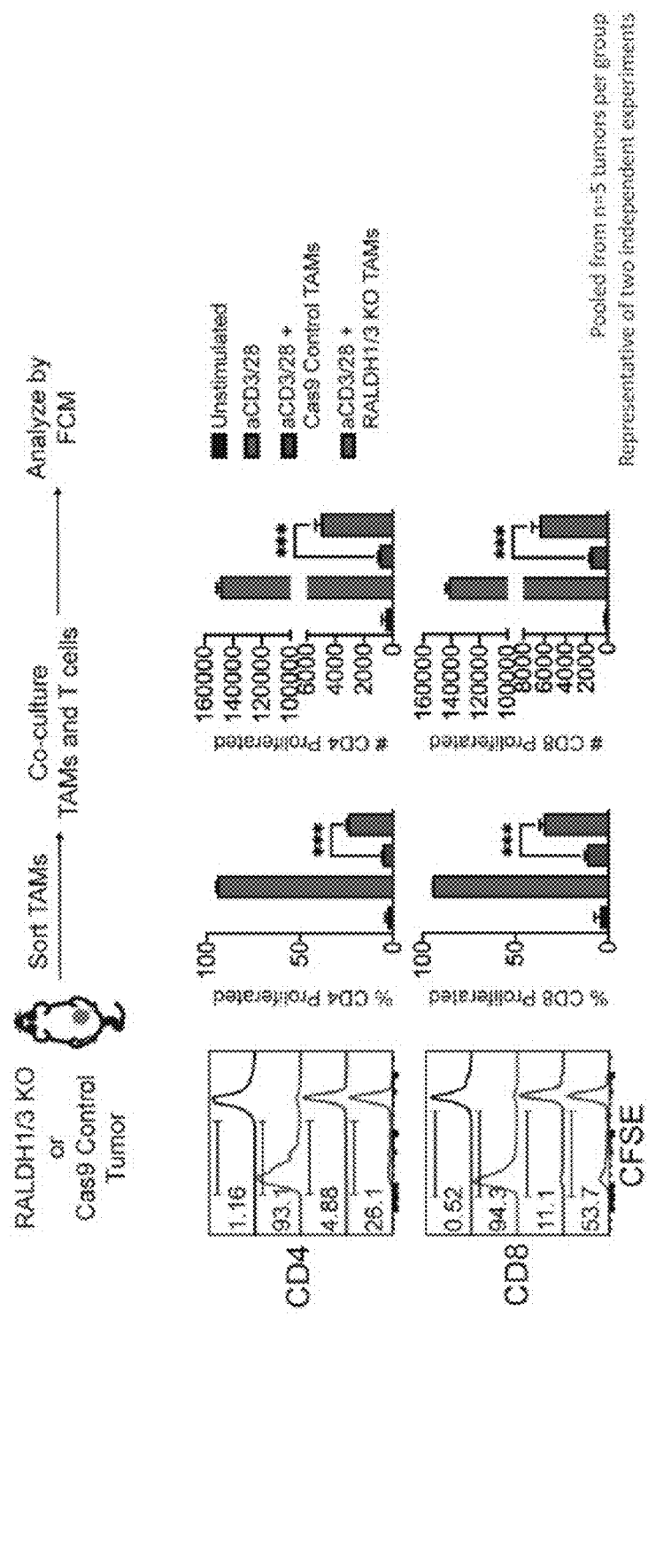
FIG. 29 illustrates that inhibiting tumor-derived RA decreases suppressive macrophage generation in vivo. T cell suppression assay using TAMs sorted from RALDH1/3 DKO or Cas9 Control tumors. Sorted TAMs were co-cultured with CFSE labeled and anti-CD3/28 stimulated splenic T cells obtained from a non-tumor bearing host. Representative histograms (left), frequencies (middle bar graph), and absolute numbers (right bar graph) of proliferated T cells are shown. Data are representative of two independent experiments.

Example 9-Inhibiting Tumor-Derived RA Decreases Suppressive Macrophage Generation In Vivo The results are show in FIG. 28 and FIG. 29. FIG. 28: Top left panel shows the frequency of CD11b+F4/80+tumor-associated macrophages (TAMs) in RALDH1/3 DKO or Cas9 Control FS tumors. Top right bar graph shows the frequency of TAMs (n=8 tumors per group). Data are representative of three independent experiments. The bottom left panel shows the frequency of TAMs expressing both CD11c and MHCII (pregated on CD11b+F4/80+) in RALDH1/3 DKO or Cas9 Control FS tumors. Bottom right panel shows the frequency of these cells (n=8 tumors per group). Data are representative of three independent experiments. FIG. 29: T cell suppression assay using TAMs sorted from RALDH1/3 DKO or Cas9 Control tumors. Sorted TAMs were co-cultured with CFSE labeled and anti-CD3/28 stimulated splenic T cells obtained from a non-tumor bearing host. Representative histograms (left), frequencies (middle bar graph), and absolute numbers (right bar graph) of proliferated T cells are shown. Data are representative of two independent experiments.

Example 10-Inhibiting Tumor-Derived RA Increases Frequency of CD11b DCs In Vivo

Figure 30:
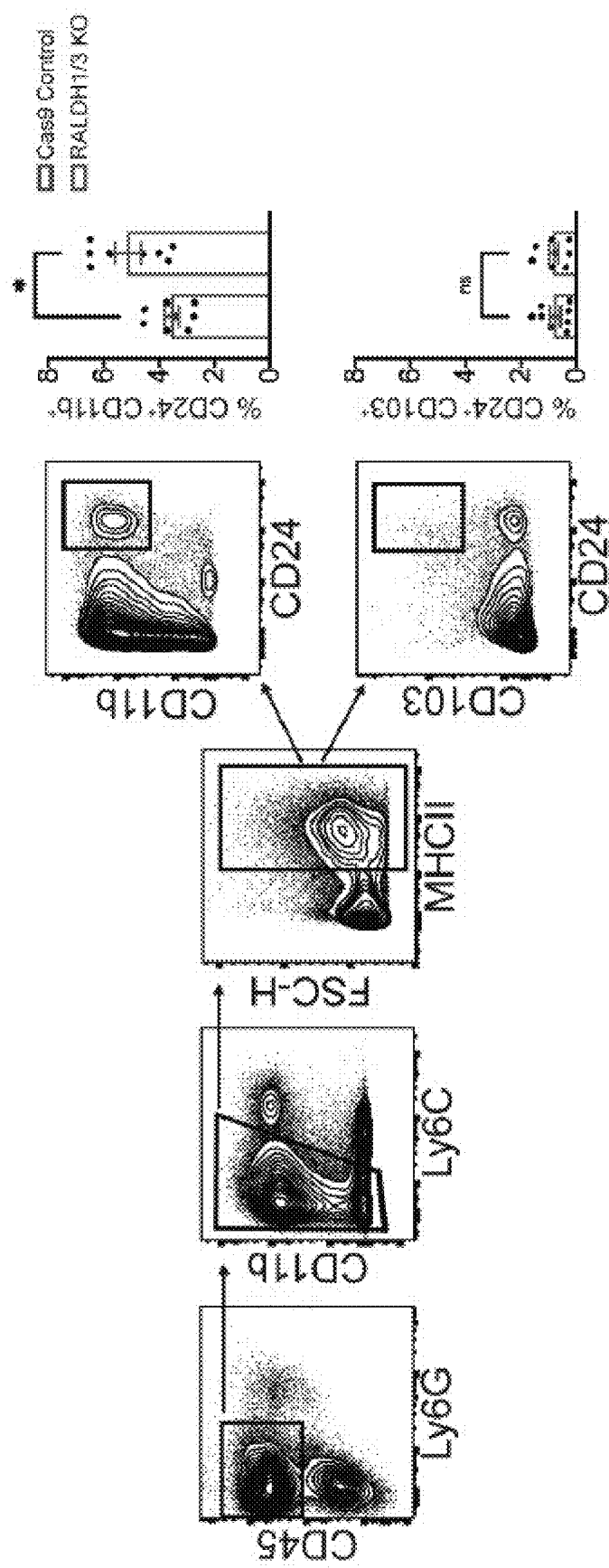
FIG. 30 illustrates that inhibiting tumor-derived RA increases frequency of CD11b DCs in vivo. Gating strategy to identify CD11b+ and CD103+DC subsets in FS tumors. The bar graph on the right shows the frequency of CD11b+ or CD103+DCs in RALDH1/3 DKO or Cas9 Control tumors (n=8 tumors per group). Data are representative of three independent experiments.

The results are shown in FIG. 30. Gating strategy to identify CD11b+ and CD103+DC subsets in FS tumors is shown. The bar graph on the right shows the frequency of CD11b+ or CD103+DCs in RALDH1/3 DKO or Cas9 Control tumors (n=8 tumors per group). Data representative of three independent experiments.

Example 11-RALDH1/3 KO Synergizes with PD-1 Blockade

Figure 31:
FIG. 31 illustrates that RALDH1/3 KO synergizes with PD-1. Anti-PD1 (or isotype control antibody) was administered to C57BL/6 mice starting at 7d post-implantation of RALDH/3 DKO or Cas9 Control FS tumors. Three doses (200 µg intraperitoneal) at Day 7, 10 and 13 were given. The graph on left shows tumor growth curves. On right is shown waterfall plots of change in tumor volume at day 12.
Figure 32:
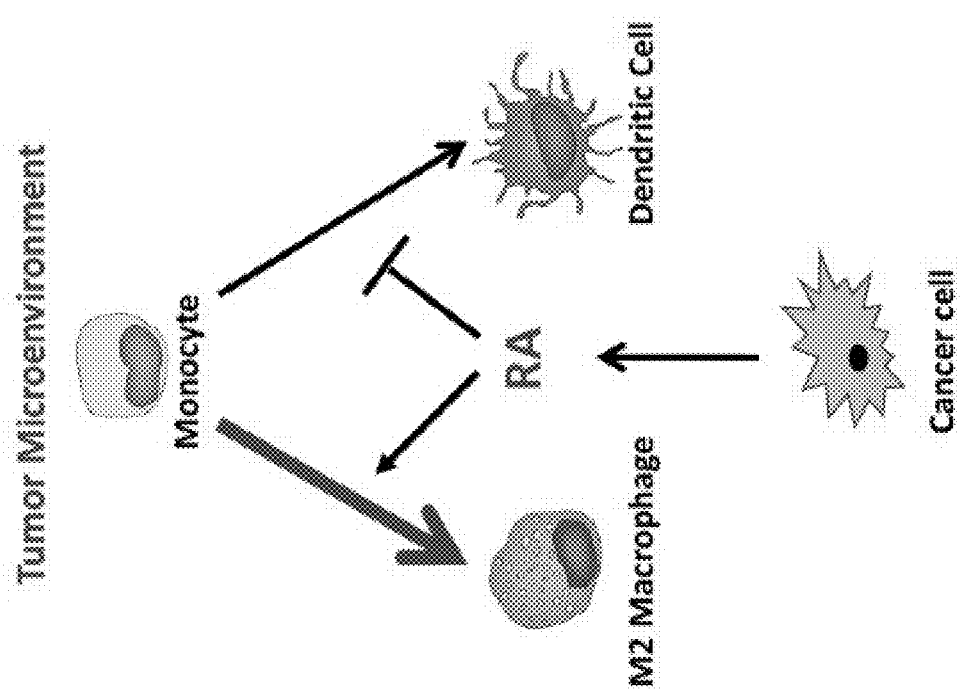
FIG. 32 is a schematic illustrating the tumor microenvironment.

The results are shown in FIG. 31. Anti-PD1 (or isotype control antibody) was administered to C57BL/6 mice starting at 7d post-implantation of RALDH1/3 DKO or Cas9 Control FS tumors. Three doses (200 ug intraperitoneal) at Day 7, 10 and 13 were given. The graph on the left of FIG. 31 shows tumor growth curves. On the right are shown waterfall plots of change in tumor volume at day 12.

Example 12-Effect of RA-Signaling Blockade on Murine Fibrosarcomas

Figures 33A, 33B:
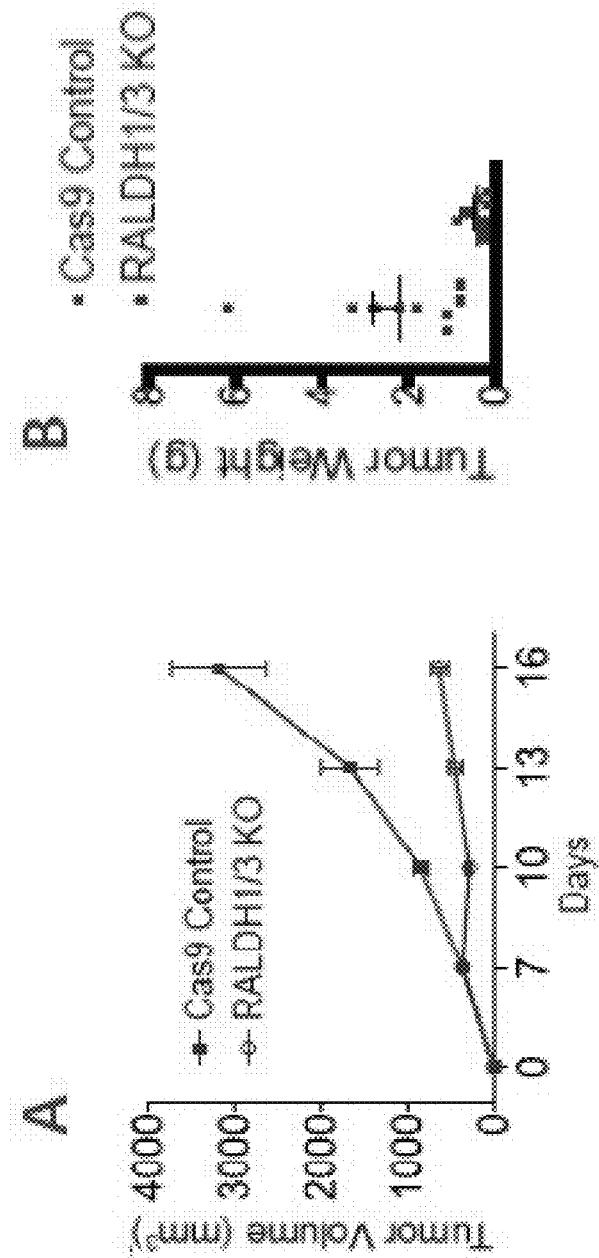
FIGS. 33A-33E illustrate the effect of RA-signaling blockade on murine fibrosarcomas. Murine fibrosarcoma cells (MCA) were transplanted into syngeneic C57BL/6J mice in all experiments shown here.
Figures 33C, 33D:
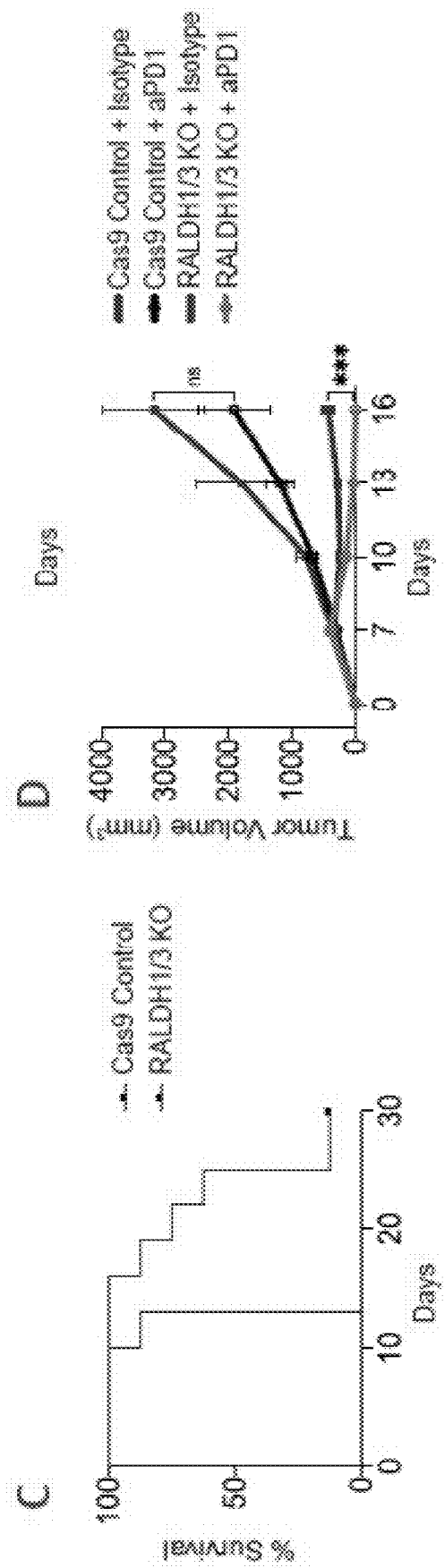
Figure 33E:
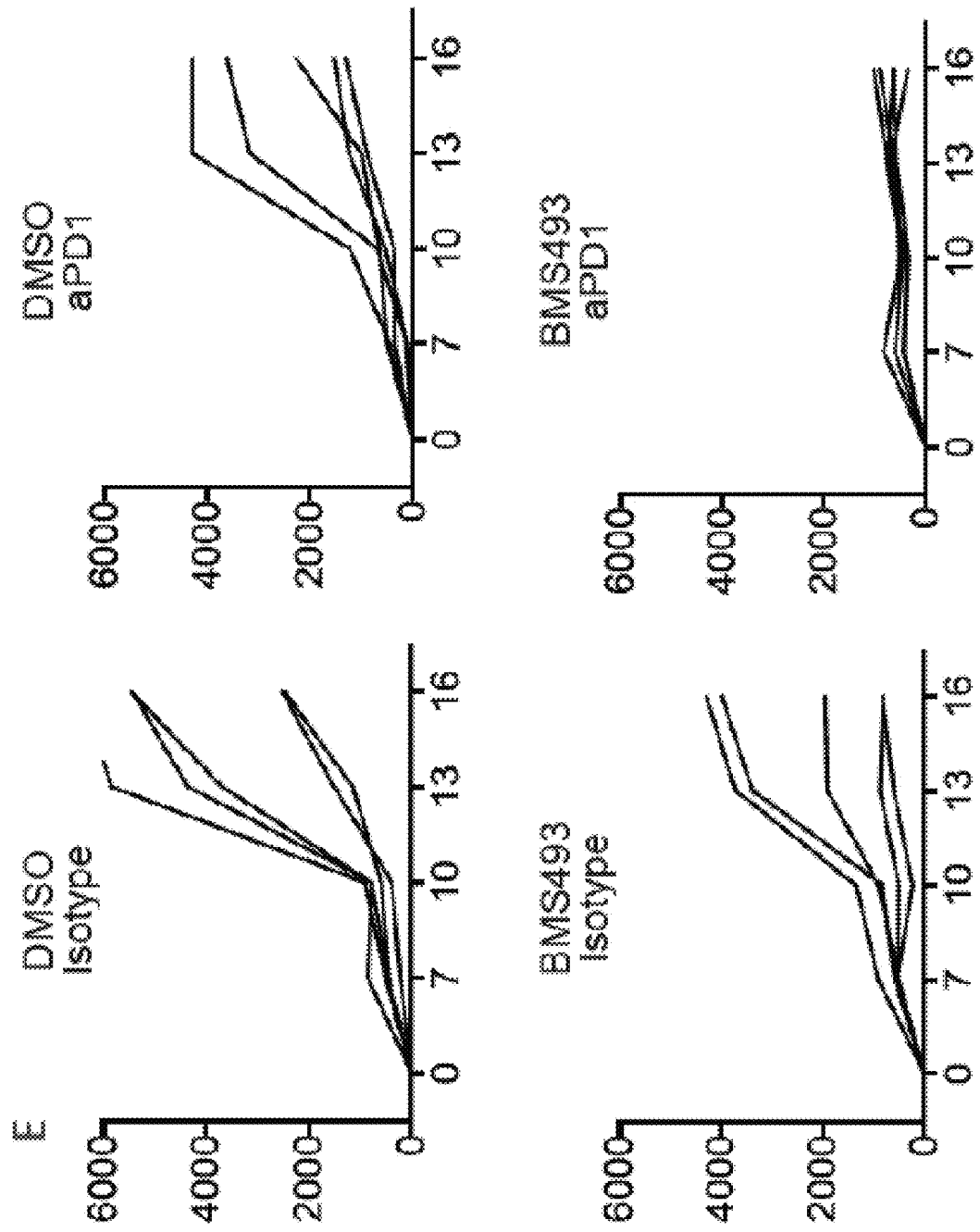

The results are shown in FIGS. 33A-33E. Tumor growth curve (FIG. 33A) or tumor weight (FIG. 33B) of RALDH1/3 DKO or Cas9 Control FS tumors implanted subcutaneously into C57BL/6 mice. Tumor volume was measured every three days starting at 7d post-implantation (n=8 tumors per group; data are representative of three independent experiments). FIG. 33C shows a survival curve of mice bearing RALDH1/3 DKO or Cas9 Control FS tumors implanted subcutaneously in C57BL/6 mice (n=12 tumors per group; data are aggregated from three independent experiments). FIG. 33D shows anti-PD1 (or isotype control antibody) was administered to C57BL/6 mice starting 7d post-implantation of RALDH1/3 DKO or Cas9 control tumors. Three doses (200 ug i.p.) at Day 7, 10 and 13 were given. Shown are the tumor growth curves. FIG. 33E shows individual growth curves of FS tumors treated with aPD1 (or isotype control) in combination with intratumoral BMS493 (or DMSO). (n=5 tumors per group).

Example 13-RA Score

Human and mouse primary monocytes were cultured in GM-CSF+IL4 to generate DCs. At the onset of the culture, retinoic acid was added to some samples. RNA was extracted 24 hours after the addition of retinoic acid (or control solution). Microarray based gene expression profiling was performed using affymetrix arrays. Genes induced or suppressed upon RA exposure were identified. This list of 'RA-regulated genes' was used to calculate an 'RA-score.' This RA score was tested on publicly available TCGA gene expression datasets from multiple human tumors to identify cancers that may produce high levels of RA for immune escape.

OTHER EMBODIMENTS

The recitation of a listing of elements in any definition of a variable herein includes definitions of that variable as any single element or combination (or subcombination) of listed elements. The recitation of an embodiment herein includes that embodiment as any single embodiment or in combination with any other embodiment or portions thereof.

The disclosures of each and every patent, patent application, and publication cited herein are hereby incorporated herein by reference in their entirety. While this invention has been disclosed with reference to specific embodiments, it is apparent that other embodiments and variations of this invention may be devised by others skilled in the art without departing from the true spirit and scope of the invention. The appended claims are intended to be construed to include all such embodiments and equivalent variations.

What is claimed is:

1. A method for treating a patient having a solid tumor, the method comprising administering to the patient an effective amount of a retinoic acid receptor inhibitor, an immune checkpoint inhibitor, and an inhibitor of an enzyme in the retinoic acid biosynthesis pathway.

2. The method of claim 1, wherein the retinoic acid receptor inhibitor is selected from the group consisting of AGN 193109, BMS 195614, BMS 493, CD 2665, ER 50891, LE 135, LY 2955303, MM 11253, any salt or solvate thereof, and any combinations thereof.

3. (c) The method of claim 1, wherein the immune checkpoint inhibitor is selected from the group consisting of an anti-PD1 antibody, an anti-PD-L1 antibody, an anti-CTLA4 antibody, any fragment thereof, and any combinations thereof.

4. The method of claim 1, further comprising administering to the patient an anti-IL13 antibody or fragment thereof.

5. The method of claim 1, wherein the retinoic acid receptor inhibitor, the immune checkpoint inhibitor, and the inhibitor of an enzyme in the retinoic acid biosynthesis pathway are administered to the patient simultaneously or sequentially.

6. The method of claim 4, wherein the retinoic acid receptor inhibitor, the immune checkpoint inhibitor, the inhibitor of an enzyme in the retinoic acid biosynthesis pathway, and the anti-IL13 antibody or fragment thereof are administered to the patient simultaneously or sequentially.

7. The method of claim 1, wherein the retinoic acid receptor inhibitor, the immune checkpoint inhibitor, and the inhibitor of an enzyme in the retinoic acid biosynthesis pathway further comprise a pharmaceutically acceptable carrier or adjuvant.

8. The method of claim 6, wherein the retinoic acid receptor inhibitor, the immune checkpoint inhibitor, the inhibitor of an enzyme in the retinoic acid biosynthesis pathway, and the anti-IL13 antibody or fragment thereof further comprise a pharmaceutically acceptable carrier or adjuvant.

9. The method of claim 1, wherein the solid tumor is a sarcoma.

10. A composition comprising:
a. a retinoic acid receptor inhibitor;
b. an immune checkpoint inhibitor; and
c. an inhibitor of an enzyme in the retinoic acid biosynthesis pathway.

11. The composition of claim 10, further comprising an anti-IL13 antibody.

12. The composition of claim 10, wherein the immune checkpoint inhibitor is selected from the group consisting of an anti-PD1 antibody, an anti-PD-L1 antibody, an anti-CTLA4 antibody, any fragment thereof, and any combinations thereof.

13. The method of claim 1, wherein the enzyme in the retinoic acid biosynthesis pathway is selected from the group consisting of RALDH1, RALDH2 and RALDH3.

14. The method of claim 1, wherein the enzyme in the retinoic acid biosynthesis pathway is RALDH1.

15. The method of claim 1, wherein the retinoic acid receptor inhibitor is administered intratumorally.

16. The composition of claim 10, wherein the enzyme in the retinoic acid biosynthesis pathway is selected from the group consisting of RALDH1, RALDH2 and RALDH3.

17. The composition of claim 10, wherein the enzyme in the retinoic acid biosynthesis pathway is RALDH1.

\* \* \* \* \*